US007790153B2

(12) United States Patent
Brod

(10) Patent No.: US 7,790,153 B2
(45) Date of Patent: Sep. 7, 2010

(54) METHOD OF TREATING RHEUMATOID ARTHRITIS USING ORALLY ADMINISTERED TYPE ONE INTERFERONS

(75) Inventor: Staley Brod, Houston, TX (US)

(73) Assignee: Research Development Foundation, Carson City, NV (US)

( * ) Notice: Subject to any disclaimer, the term of this patent is extended or adjusted under 35 U.S.C. 154(b) by 1758 days.

(21) Appl. No.: 10/801,277

(22) Filed: Mar. 16, 2004

(65) Prior Publication Data

US 2004/0151694 A1 Aug. 5, 2004

Related U.S. Application Data

(63) Continuation-in-part of application No. 08/946,710, filed on Oct. 8, 1997, now abandoned.

(51) Int. Cl.
*A61K 38/21* (2006.01)
*C07K 17/00* (2006.01)
*A61K 38/19* (2006.01)

(52) U.S. Cl. ................ 424/85.7; 530/351; 424/85.1

(58) Field of Classification Search .................. None
See application file for complete search history.

(56) References Cited

U.S. PATENT DOCUMENTS

| 4,409,243 A | 10/1983 | Lieb | 424/330 |
|---|---|---|---|
| 4,462,985 A | 7/1984 | Cummins | 424/85 |
| 4,497,795 A | 2/1985 | Cummins | 424/85.6 |
| 5,019,382 A | 5/1991 | Cummins | 424/85.4 |
| 5,093,338 A | 3/1992 | Byrne | 514/291 |
| 5,624,895 A | 4/1997 | Sobel | 514/8 |
| 5,780,021 A | 7/1998 | Sobel | 424/85.4 |

FOREIGN PATENT DOCUMENTS

| WO | WO 83/03411 | 10/1983 |
|---|---|---|
| WO | WO 94/20122 | 9/1994 |
| WO | WO 96/28183 | 9/1996 |

OTHER PUBLICATIONS

Shiozawa et al. A preliminary study on the effect of alpha-interferon treatment on the joint inflammation and serum calcium in rheumatoid arthritis (1992), British J. of Rheumatology, vol. 31, pp. 405-408.*
Aman et al. Regulation of cytokine expression by interferon-alpha in human bone marrow stromal cells: inhibition of hematopoietic growth factors and induction of interleukin-1 receptor antagonist (1994), Blood, vol. 84, pp. 4142-4150.*
"Interferon beta-1b is effective in relapsing-remitting multiple sclerosis. I. Clinical results of a multicenter, randomized, double-blind, placebo-controlled trial. The IFNB Multiple Sclerosis Study Group," *Neurology* 43:655-661. 1993.
Bayley et al., "The transmucosal absorption of recombinant human interferon-alpha B/D hybrid in the rat and rabbit," *J. Pharm. Phramacol.* 47(9):721-724. 1995.
Bocci et al., "Is interferon effective after oral administration? The state of the art." *J. Biol. Regul. Homeos. Agents*, 4(2):81-83, 1990.

Bocci, "Absorption of cytokines via oropharyngeal-associated lymphoid tissues," *Clin Pharmacokinet*, 21(6):411-417, 1991.
Bocci, "Immunomodulators as local hormones: new insights regarding their clinical utilization," *Journal of Biological Response Modifiers*, 4:340-352, 1985.
Bosio et al., "Efficacy of low-dose oral use of type I interferon in cytomegalovirus infections in vivo," *J. Interferon Cytokine Res.*, 19:869-876, 1999.
Brod and Khan "Oral administration of IFN-α is superior to subcutaneous administration of IFN-α in the suppression of chronic relapsing experimental autoimmune encephalomyelitis," *J. Autoimmunity*, 9:11-20, 1996.
Brod et al., "Ingested (oral) IFN-alpha induces MxA mRNA in RRMS" (Submitted for publication).
Brod et al., "Ingested IFN-α has biological effects in humans with relapsing-remitting multiple sclerosis," *Mult. Scler.*, 3:1-7, 1997.
Brod et al., "Ingested interferon α suppresses type I diabetes in non-obese diabetic mice," *Diabetologia*, 41:1227-1232, 1998.
Brod et al., "Ingested interferon alpha induces Mx mRNA," *Cytokine*, 11:1-8, 1999.
Brod et al., "Ingested interferon alpha preserves residual best cell function type 1 diabetes," *J. Interferon Cytokine Res.*, 2(12):1021-1030, 2001.
Brod, "Hypothesis: multiple sclerosisis a type I interferon deficiency syndrome," *Proc. Soc. Exp. Biol. Med.* 218:278-283, 1998.
Butcher, "The regulation of lymphocyte traffic," *Current Topics in Microbiology and Immunology*, 128:85-122, 1986.
Cantell and Pyhala, "Circulating interferon in rabbits after administration of human interferon by different routes," *Virol*, 20:97-104, 1973.
Carter et al., "Disease modifying therapies in multiple sclerosis," *CNS Drugs*, 3:99-114, 1995.
Connelly, "Interferon beta for multiple sclerosis," *Ann. Pharmacother.*, 28(5):610-616, 1994.
Dhingra et al., "A phase-I clinical study of low-dose oral interferon-alpha," *J. Immunother.*, 14(1):51-55, 1993.
Fleischmann et al., Orally administered interferons exert their white blood cell suppressive effects via a novel mechanism, *Neurology*, 13, 1993.
Gibson et al., "Pharmacokinetics of recombinant leukocyte A interferon following various routes and modes of administration to the dog," *Journal of Interferon Research*, 5:403-408, 1985.

(Continued)

*Primary Examiner*—Christine J Saoud
*Assistant Examiner*—Jegatheesan Seharaseyon
(74) *Attorney, Agent, or Firm*—Fulbright & Jaworski LLP

(57) ABSTRACT

The present invention provides a method of treating autoimmune diseases in an animal comprising the step of orally administering a type one interferon to said animal. Also provided is a method of reducing inflammation associated with an auto-immune disease in an animal comprising the step of orally administering a type one interferon to said animal. Further provided is a method of decreasing the levels of a cytokine in an individual having multiple sclerosis, comprising the step of orally administering a type one interferon to said individual, wherein said cytokine is selected from the group consisting of TGF-β, IL-2, IL-10, IFN-γ and the inflammatory soluble serum marker ICAM-1. In addition, the present invention provides a method of decreasing the incidence of insulin-dependent diabetes mellitus in at-risk populations, comprising the step of orally administering INF-α to individuals of said at-risk population.

12 Claims, 23 Drawing Sheets

OTHER PUBLICATIONS

Giron et al., "Effect of interferons and poly(I):poly(C) on the pathogenesis of the diabetogenic variant of encephalomyocarditis virus in different mouse strains," *J. Interferon Res*, .8(6):745-753. 1988.

Goldsteein et al., "Human biologic response modification by interferon in the absence of measurable serum concentrations: a comparative trial of subcutaneous and intravenous interferon-β serine," *Journal of the National Cancer Institute*, 81(14):1061-1068, 1989.

Goodkin et al., "Experimental therapies for multiple sclerosis: current status," *Cleve. Clin. J. Med.*, 59:63-74. 1992.

Gross et al., "Interferon-α with condylomata acuminata and juvenile diabetes mellitus," *Deutsche Medizinische Wochenschrift*, 111(36):1351-1355, 1986. (Abstract).

Higgins et al., "Suppression of experimental autoimmune encephalomyelitis by oral administration of myelin basic protein and its fragments," *J. Immunol.* 140:440-445, 1988.

Horisberger, MX protein: function and mechanism of action, *Biotechnolgy*, Ciba-Geigy Ltd., CH-4002 Basel, Switzerland.

Hutchison et al., "Chronic recurrent aphthous stomatitis: oral treatment with low-dose interferon alpha," *Mol. Biother.*, 2:160-164, 1990.

Koech et al., "Efficacy of Kemron (low dose oral natural human interferon alpha) in the management of HIV-1 infection and acquired immune deficiency syndrome (AIDS)," *East Afr. Med. J.*, 67(7 Supp 2):SS64-70, 1990.

Koech et al., "Low dose oral alpha-interferon therapy for patients seropositive for human immunodeficiency virus type-1 (HIV-1)," *Mol. Biother.*, 2(2):91-95. 1990.

Konrad et al., *Biological Barriers to Protein Delivery*, ch. 14, 409-437, ed. Audus et al. 1993.

Larocca et al., "Evaluation of neutralizing antibodies in patients treated with recombinant interferon-β ser," *Journal of Interferon Research*, 9(Supp 1):S51-S60, 1989.

Lecce et al., "Treatment of rotavirus infection in neonate and weanling pigs using natural human interferon alpha," *Mol. Biother.* 2(4):211-216, 1990.

Liu et al., "Accumulation of protein O-GlcNAc modification inhibits proteasomes in the brain and coincides with neuronal apoptosis in brain areas with high O-GlcNAc metabolism," *J. Neurochem*, .89(4):1044-1055.

Mashkovskii et al., "Drugs," Moscow, Meditsina, 2:389-392, 1993.

Mowat et al., "The regulation of immune responses to dietary protein antigens," *Immun. Today*, 8:93-98, 1987.

Nagler et al., "Immunotherapy with recombinant human interleukin-2 and recombinant interferon-alpha in lymphoma patients postautologous marrow or stem cell transplant," *Blood*, 89:3951-5959.

Owens et al., "The immunology of multiple sclerosis and its animal model, experimental allergic encephalomyelitis," *Neurol. Clin*, 13(1):51-73, 1995.

Paulesu et al., "Oral administration of human recombinant interferon-a2 in rats," Elsevier Science Publishers B.V. (Biomedical Division), 46:199-202, 1988.

Radwanski et al., "Pharmacokinetics of interferon α-2b in healthy volunteers," *J Clin Pharmacol*, 27:432-435, 1987.

Satoh et al., "Suppression of late asthmatic response by low-dose oral administration of interferon-beta in the guinea pig model of asthma," *J. Interferon Cytokine Res.*, 19:887-894, 1999.

Schafer et al., "Interferon administered orally: protection of neonatal mice from lethal virus challenge," *Science*, 176:1326-1327, 1972.

Shibutani et al., "Toxicity studies of human fibroblast interferon beta (I) acute and subacute toxicity studies in mice and rats," *Iyakuhin Kenkyu*, 18:571-582. (1987) (Abstract).

Shim et al., "Administration route dependent bioavailability of interferon-α and effect of bile salts on the nasal absorption," *Drug Dev. Indus. Pharm.*, 19:1183-1199. 1993.

Thompson et al., "Gastric administration of type II collagen delays the onset and severity of collagen-induced arthritis in rats," *Clin. Exp. Immunol.*, 64(3):581-586, 1985.

Vial et al., "Clinical toxicity of the interferons," *Drug Saf.*, 10(2):115-150, 1994.

Wedner et al., *Basic Clinical Immunology*, 7$^{th}$ edition Chap 34, 1991.

Wills et al., "Pharmacokinetics of recombinant alpha A interferon following IV infusion and bolus, IM, and PO administration to African green monkeys," *Journal of Interferon Research*, 4(3):399-409, 1984.

Witt et al., "Absence of biological effects of orally administered interferon-βser," *Journal of Interferon Research*, 12:411-413, 1992.

Yershov et al., "Interferon status in different diseases," *Voprosy Virusologii*, 35:444-448, 1990 (Russian).

\* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: artificial sequence
<220> FEATURE:
<221> NAME/KEY: primer_bind
<222> LOCATION: 400..420
<223> OTHER INFORMATION: Mx plus strand

<400> SEQUENCE: 1
gtggagcagg acctggccct g                                                   21

<210> SEQ ID NO 2
<211> LENGTH: 20
<212> TYPE: DNA
<213> ORGANISM: artificial sequence
<220> FEATURE:
<221> NAME/KEY: primer_bind
<222> LOCATION: 895..876
<223> OTHER INFORMATION: Mx minus strand

<400> SEQUENCE: 2
gtaacggtgg tgtctccgag                                                     20

<210> SEQ ID NO 3
<211> LENGTH: 25
<212> TYPE: DNA
<213> ORGANISM: artificial sequence
<220> FEATURE:
<221> NAME/KEY: primer_bind
<222> LOCATION: 84..108
<223> OTHER INFORMATION: G3PDH plus strand

<400> SEQUENCE: 3
caacggattt ggtcgtattg ggcgc                                               25

<210> SEQ ID NO 4
<211> LENGTH: 25
<212> TYPE: DNA
<213> ORGANISM: artificial sequence
<220> FEATURE:
<221> NAME/KEY: primer_bind
<222> LOCATION: 1068..1094
<223> OTHER INFORMATION: G3PDH minus strand

<400> SEQUENCE: 4
ccgggtgtac cggaggttcc tcatt                                               25

<210> SEQ ID NO 5
<211> LENGTH: 20
<212> TYPE: DNA
<213> ORGANISM: artificial sequence
<220> FEATURE:
<221> NAME/KEY: primer_bind
<222> LOCATION: 405..425
<223> OTHER INFORMATION: MxA primer

<400> SEQUENCE: 5
accagatccc tctggtgctg                                                     20

<210> SEQ ID NO 6
<211> LENGTH: 25
<212> TYPE: DNA
<213> ORGANISM: artificial sequence
```

-continued

```
<220> FEATURE:
<221> NAME/KEY: primer_bind
<222> LOCATION: 687..663
<223> OTHER INFORMATION: GAPDH primer

<400> SEQUENCE: 6
ccgtccctac tacaagacct ctcgg                                           25
```

METHOD OF TREATING RHEUMATOID ARTHRITIS USING ORALLY ADMINISTERED TYPE ONE INTERFERONS

CROSS-REFERENCE TO RELATED APPLICATION

This is a continuation of application U.S. Ser. No. 08/946,710 filed on Oct. 8, 1997, now abandoned, which claims benefit of priority under 35 U.S.C. 120 of U.S. Ser. No. 08/844,731, filed Apr. 21, 1997, which claims benefit of priority under 35 U.S.C. 120 of U.S. Ser. No. 08/631,470, filed Apr. 12, 1996, which claims benefit of priority under 35 U.S.C. 120 of U.S. Ser. No. 08/408,271, filed Mar. 24, 1995, now abandoned, which claims benefit of priority under 35 U.S.C. 120 of U.S. Ser. No. 08/226,631, filed Apr. 12, 1994, now abandoned.

BACKGROUND OF THE INVENTION

1. Field of the Invention

The present invention relates generally to the fields of neurology, immunology and protein chemistry. More specifically, the present invention relates to a novel methods of treating auto-immune diseases using type one interferons.

2. Description of the Related Art

Acute experimental autoimmune encephalomyelitis [EAE] is a T cell mediated inflammatory autoimmune process of the central nervous system which resembles the human disease multiple sclerosis. CR-EAE, a chronic inflammatory autoimmune process of the central nervous system that resembles human multiple sclerosis [MS] both in its pathological and clinical expression, provides a model to assess interventions to alter the course of a human autoimmune disease. Myelin basic protein [MBP] is an important neuroantigen in the pathogenesis of this disease. CR-EAE in SJL/J mice can b e adoptively transferred following the intravenous injection of an MBP peptide 89-100 specific T cell line. Coculture of MBP peptide 91-103 specific T cells with chemically crosslinked peptide renders the T cells tolerant to MBP in CR-EAE in the SJL/J mouse.

Parenteral, e.g., IV administration of natural rat interferon [$10^5$ units] partially suppresses acute EAE in male Lewis rats and inhibits passive hyperacute localized EAE when administered on the same day of immunogen inoculation. Other parenterally administered cytokines such as TGF-β can decrease clinical disease and inflammation in brain and spinal cord in EAE. Parenterally administered natural human IFN-α can decrease T cell function and T cell dependent antibody production in humans. Orally administered natural human IFN-α can prevent experimental development of viral and parasitic infections in animals. Acute EAE provides a model to demonstrate the ability of orally administered immunoactive substances to influence the course of an autoimmune disease.

Human IFN-α is an immunoactive protein that can b e orally administered at low doses in the treatment of viral disease in animals. Human IFN-β, another type 1 interferon, augments suppressor cell function in vitro in progressive MS and rat IFN-β decreases the severity of symptoms in rat EAE. In view of the immunoregulatory and anti-viral properties of the type 1 interferons, its response and production has been assessed in autoimmune diseases. Inactive rheumatoid arthritis is marked by augmented [2'-5'] oligoadenylate synthetase [OAS], a readily assayed measurement of type 1 interferon activity, in peripheral blood leucocytes secondary to an IFN-α/β stimulus; active rheumatoid arthritis exhibited a significantly reduced IFN-α/β production compared to normal donors. Other autoimmune diseases, such as psoriasis and atopic dermatitis, also showed decreased interferon production. Peripheral blood lymphocytes in patients with MS show a similar ineffective production of type 1 interferons in response to viral or mitogenic stimulus which parallels the severity of the disease. Natural killer [NK] cell activity is deficient in MS, which is correlated with disease severity, and can be normalized with IFN-α treatment.

The reported abnormalities of production or response to type 1 interferon in autoimmune diseases have prompted several small pilot studies using type 1 interferons as therapeutic agents in MS. These studies used systemic administered type 1 interferon in doses of 1 million units or more daily without significant clinical improvement. A study of parenterally administered IFN-β in relapsing-remitting MS suggests that 1.6-8 million units of IFN-β s.c., three times per week, can decrease relapses by 40-50% and decrease brain inflammation as assessed by serial MRI.

Additionally, rheumatoid arthritis (RA) is a common chronic disorder involving the synovial membranes of multiple joints that is considered by most to be an autoimmune disease. Within joints of patients with rheumatoid disease, chronic (lymphocyte mediated) or acute (lymphocyte and polymorph mediated) tissue inflammation are the predominant mechanisms leading to tissue changes in synovial joints (Cruikshank, 1954). In light of th e research performed in conjunction with the present series of applications, an open label phase I study was performed with ingested IFN-α to determine the safety, clinical effects on joint disease, and potential modulation of proinflammatory cytokine secretion in subjects with RA.

Insulin-dependent diabetes mellitus (IDDM) is a chronic disorder that results from autoimmune destruction of the insulin-producing pancreatic b cell. In the United States, the prevalence of IDDM by age 20 years is 0.26% and lifetime prevalence approaches 0.40%; thus approximately one million Americans have IDDM. Histologic studies suggest that an 80% reduction in the volume of b cells is required to induce symptomatic IDDM. The nonobese diabetic (NOD) mouse is a model of the human autoimmune disease. Many key features of human IDDM are reflected in the NOD mouse model; the development of insulinitis with infiltration of lymphocytes into the pancreatic islets of Langerhans that are selectively cytotoxic to the insulin producing b cells; the dependence of disease pathogenesis by T cells; transmission of IDDM by hematopoietic cells in bone marrow.

The NOD mouse model is mechanistically analogous to the EAE animal model because they are both presumed to be T cell subset mediated, dependent on restriction elements and inflammatory cytokines for disease expression. Although neither acute or chronic EAE have exact parallels to the NOD model, their similarities suggest that interventions successful in EAE can have therapeutic efficacy in the NOD mouse. Both IDDM and EAE can be induced by T cells, primarily one of the two types of helper T cells—T helper cells type 1 (Th1) which produce pro-inflammatory cytokines such as IL-2, IFN-γ or TNF-α. In contrast, administration or up-regulation of the Th2-associated cytokines IL-4 and IL-10 is beneficial and can ameliorate autoimmune disease.

The prior art is deficient in the lack of effective means of treating auto-immune diseases by oral administration of cytokines, such as type one interferons. The present invention fulfills this longstanding need and desire in the art.

SUMMARY OF THE INVENTION

It is an object of the present invention to show that the oral administration of a type one interferon inhibits proliferation to sensitized antigens, suppresses the clinical expression of relapses, and decreases inflammation via alteration of cytokines in murine CR-EAE.

It is another object of the present invention to illustrate the effect of type one interferons orally administered before an d after immunization with GP-MBP in acute EAE.

It is another object of the present invention to suppress the clinical expression of attacks of autoimmune disease, decrease pathological sequellae and inhibit inflammatory cytokines in such diseases by the oral administration of biological response modifiers such as type one interferons.

It is also an object of the present invention to show the effect of oral rat IFN-α/β on clinical outcome, histology and IFN-γ secretion in experimental allergic neuritis, the in vivo model of acute inflammatory demyelinating radiculoneuropathy or Guillain-Barré syndrome.

In one embodiment of the present invention, there is provided a method of treating auto-immune diseases in an animal comprising the step of orally administering a type one interferon to said animal.

In another embodiment of the present invention, there is provided a method of decreasing the severity or frequency of a relapse of multiple sclerosis in a human comprising the step of orally administering a type one interferon to said animal.

In yet another embodiment of the present invention, there is provided a method of reducing inflammation associated with an auto-immune disease in an animal comprising the step of orally administering a type one interferon to said animal.

In still yet another embodiment of the present invention, there is provided a method of inhibiting the onset of an auto-immune disease comprising the step of orally administering a type one interferon to said animal.

In yet another embodiment of the present invention, there is provided a method of decreasing the incidence of insulin-dependent diabetes mellitus in at-risk populations, comprising the step of orally administering INF-α to individuals of said at-risk population.

Parenterally administered human recombinant type I interferons [hrIFN] in relapsing-remitting multiple sclerosis [RRMS] decrease relapses and spontaneous in vitro IFN-γ production, reduce clinical progression, and decrease magnetic resonance imaging (MRI)-defined disease activity and lesions. Because parenterally administered type I IFN use is limited by clinical and chemical toxicities and the induction of antibodies that abrogate their activity and correlate with the loss of clinical benefit, whether ingested IFN-α was non-toxic and had biological effects in humans was determined. A significant decrease in CD3-mediated IFN-γ secretion was seen post-treatment in normal controls ingesting 30,000 units IFN-α but not those ingesting 300, 1,000, 3,000, 10,000 or 100,000 units. In subjects with relapsing-remitting multiple sclerosis, a significant decrease in Con A-mediated proliferation and serum soluble intercellular adhesion molecule-1 (sICAM-1), a surrogate measure for disease activity in MS, was found after ingesting 10,000 and 30,000 units IFN-α. The relapsing-remitting multiple sclerosis subjects also showed decreased Con A-induced IL-2 secretion after ingesting 10,000 units IFN-α, and decreased Con A-induced IFN-γ, TGF-β, IL-10 production and decreased CD3-induced IL-10 production after ingesting 30,000 units IFN-α. The present invention shows that ingested human IFN-α is a profound biological response modifier in humans.

Thus, in another embodiment of the present invention, there is provided a method of decreasing the levels of a cytokine in an individual having multiple sclerosis, comprising the step of orally administering a type one interferon to said individual, wherein said cytokine is selected from the group consisting of TGF-β, IL-2, IL-10, IFN-γ and, a marker for inflammation, ICAM-1. Preferably, the interferon is administered in a dosage of from about 166 I.U./kg to about 500 I.U./kg.

Finally, in yet another embodiment of the present invention, there is provided a method of decreasing the levels of a cytokine in an individual having rheumatoid arthritis, comprising the step of orally administering a type one interferon to said individual, Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
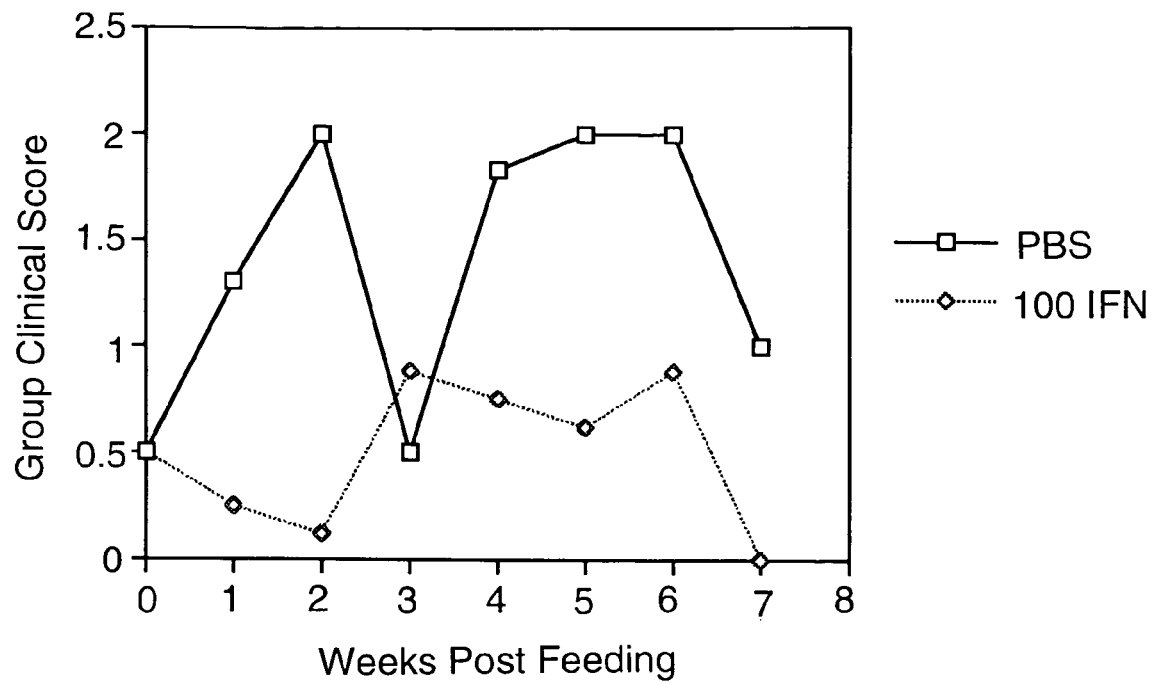
FIG. 1 shows that orally administered murine natural IFN-α/β suppresses clinical relapse in murine CR-EAE. Two groups of six animals were inoculated and following the first attack were fed either mock IFN or 100 units murine natural IFN-α/β 3 times per week for seven weeks. One of two representative experiments is shown. SEM is <10%.

In the present invention, the modification of disease and inhibition of inflammatory cytokine production induced by orally administered cytokines in EAE provide a convenient, effective and long term means for treatment of autoimmune diseases of unknown antigen in humans, in particular multiple sclerosis.

The present invention is directed to a method of treating auto-immune diseases in an animal comprising the step of orally administering a type one interferon to said animal. Generally, the interferon useful in the methods of the present invention is either alpha-interferon and beta-interferon. The type one interferon may be derived from any suitable source. Preferably, the interferon is selected from the group consisting of human recombinant interferon, rat interferon and murine interferon.

Generally, the type one interferon administered in the methods of the present invention would be administered at a dose that effectively inhibits the onset or reoccurrence, etc., of the auto-immune disease. For example, the interferon may be administered in a dosage of from about 50 I.U./kg to about 25000 I.U./kg.

The methods of the present invention may be practiced on any animal having an autoimmune disease. Most preferably, the methods of the present invention will be useful in treating humans.

A wide variety of auto-immune diseases may be treated by the methods of the present invention. Representative examples of auto-immune diseases include multiple sclerosis, rheumatoid arthritis, diabetes mellitus, psoriasis, organ-specific auto-immune diseases, chronic inflammatory demyelinating polyradiculoneuropathy and Guillain-Barré syndrome.

The present invention is also directed to a method of decreasing the severity or frequency of a relapse of multiple sclerosis in a human comprising the step of orally administering a type one interferon to said animal. Moreover, the present invention also is directed to a method of inhibiting the onset of an auto-immune disease comprising the step of orally administering a type one interferon to said animal. In particular, the present invention provides a method of decreasing the incidence of insulin-dependent diabetes mellitus in at-risk populations, comprising the step of orally administering INF-α to individuals of said at-risk population.

The following examples are given for the purpose of illustrating various embodiments of the invention and are not to limit the present invention in any fashion.

EXAMPLE 1

Induction of Experimental Autoimmune Encephalomyelitis.

A chronic relapsing form of EAE was induced in 7-10 week old female SJL/J mice using the method of Brown and McFarlin, *Lab. Invest.* (1981) 45:278-284 as modified by Miller et al., *J. Immunol.* (1987) 138:3776-3784. Briefly, each mouse received a subcutaneous injection over the shaved right flank of 0.3 ml of an emulsion containing 1 mg of syngeneic mouse spinal cord homogenate [MSCH] in 0.15 ml of phosphate buffered saline and 0.03 mg of *Mycobacterium tuberculosus hominis* H37Ra [MT] [Difco Labs, Detroit, Mich.] in 0.15 ml of incomplete Freund's adjuvant [IFA]. Seven days later, the mice received a similar injection in the left flank. Initial clinical signs of disease were seen between days 13 and 25 postimmunization. Initial clinical signs of disease were seen between days 13 and 25 postimmunization. Clinical severity of the relapse attack was graded as follows by a blinded observer: 0=no disease; 1=minimal or mild hind limb weakness; 2=moderate hind limb weakness or mild ataxia; 3=moderate to severe hind limb weakness; 4=severe hind limb weakness or moderate ataxia; 5=paraplegia with no more than moderate four limb weakness; 6=paraplegia with severe four limb weakness or severe ataxia. Animals were scored in a blinded fashion for 6-8 weeks and a cumulative weekly score was computed by averaging three scores per week [Monday, Wednesday, Friday] for each group of animals.

EXAMPLE 2

Cytokine Feeding

Following initial attack, animals were fed varying doses [1-100 units] of murine natural IFN-α/β [Cytimmune mouse IFN-α+β, $4.0 \times 10^5$ IRU/ml, Lee Biomolecular Research, Inc., San Diego, Calif.], or mock murine IFN-α/β [Cytimmune<2 IRU/ml, Lee Biomolecular Research, Inc., San Diego, Calif. {generated identically to IFN-α/β except cultures are mock induced}] using a 2.5 cm syringe fitted with a 20 gauge ball point needle [Thomas Scientific, Swedesboro, N.J.] three times per week [Monday, Wednesday, Friday] for 6-8 weeks. Mock IFN were used as control since heat denatured IFN may retain some immunological activity.

EXAMPLE 3

Preparation of Guinea Pig Myelin Basic Protein [GP-MBP]

Twenty grams of guinea pig spinal cord were added to 4.7 ml-20° C. methanol and homogenized with a tissue homogenizer. 9.4 ml-20° C. chloroform was added, homogenized an additional 2 minutes and stirred for 60 minutes at room temperature; then at 4° C. for an additional 60 minutes. The material was filtered through 2 thicknesses of sterile gauze through a chilled Buchner flask and a # 1 Whatman filter paper. The tissue cake was rinsed with 20 ml-20° C. acetone and was resuspended in 40 ml of cold ddH$_2$O; then stirred 30 minutes at 4° C., filtered a second time and resuspended in 10 ml of cold ddH$_2$O. Suspension was sonicated to facilitate resuspension of pellet in ddH$_2$O.

Tissue/H$_2$O slurry was adjusted to pH=3 with 1 N HCl and stirred overnight at 4° C. After an overnight spin, pH was readjusted to 3 and spun at 10,000×g for 15 minutes at 4° C. Supernatant was filtered through #1 Whatman paper and liquid filtrate retained. Filtrate was adjusted to pH=9 with 10 N NaOH and stirred for 60 minutes at 4° C.; then spun at 10,000×g for 15 minutes at 4° C. Supernatant volume was measured and ammonium sulfate added to a final concentration of 27.7 grams/100 ml; supernatant was stirred in cold for 30 minutes and then spun at 10,000×g for 15 minutes at 4° C. and resuspended in 1 ml ddH$_2$O. Resuspended pellet was dialyzed in small molecular weight [6-8000 MW] dialysis tubing against ddH$_2$O. Protein concentration was determined at A$_{280}$ via UV spectroscopy. To check purity of myelin basic protein preparation, a 7-20% SDS-PAGE gradient gel was prepared and stained with 0.3 M CuCl$_2$. Purity of guinea pig myelin basic protein [GP-MBP] preparation was demonstrated by an 18 kD band.

EXAMPLE 4

Lymph Node Cell and Spleen Preparation

Animals were killed 6-8 weeks after initiation of feeding and draining inguinal nodes and spleen cells were removed and single cell suspensions were made through a 90 um stainless wire meshes. Red cell lysis was performed in the spleen cell suspensions with 2 mls of ACK solution added to the pellet and the reaction allowed to continue at 5 minutes at room temperature.

EXAMPLE 5

In vitro T Cell Proliferation

Seven days following clinical relapse attack, mice were sacrificed, draining inguinal lymph nodes were pooled and cultured in vitro to determine antigen-specific T cell proliferative responses. Antigen stimulation was carried out with antigen at either 0 or 100 µg/ml [GP-MBP or MT] and mitogen stimulation with Con A at 2.5 µg/ml by incubating lymph node cells at $2\times10^5$ cells/well in RPMI [Gibco, Grand Island, N.Y.] supplemented with 10% fetal calf serum [FCS] [Whittaker Bioproducts, Walkersville, Md.], 1% sodium pyruvate [Gibco, Grand Island, N.Y.], 1% glutamine [Gibco], 1% Penicillin/Streptomycin, and 50 µM 2-mercaptoethanol. The plates were incubated at 5% $CO_2$ and humidified at 37° C. for 4 days. At that time the cells were pulsed with 2 µCi of tritiated [$^3$H] dTd and harvested 18 hours later on an automated harvester. [$^3$H] dTd uptake was measured in a Beckman [liquid] scintillation counter. Cultures were run in triplicate and the results expressed as ΔACPM.

EXAMPLE 6

Histology

Following sacrifice, spinal cords were removed and immersion fixed in 10% neutral buffered formalin for a minimum of two weeks. After fixation, brains were bisected in the horizontal plane, and cords sectioned in entirety in the horizontal plane at approximately 3 mm intervals and processed to paraffin. Paraffin blocks were sectioned at 6-8 microns, and step sections were stained with hematoxylin and eosin and with Luxol-fast blue/PAS/hematoxylin and examined by light microscopy. Cord sections were evaluated independently for foci of inflammation by a blinded observer, without knowledge of the treatment status of the animals prior to sacrifice. Spinal cord tissue was sampled in an identical fashion for each animal and numbers of parenchymal inflammatory foci per section [>20 inflammatory cells] were counted.

EXAMPLE 7

Cytokine Analysis

Spleen cells from mock and 100 unit murine IFN-α/β treated animals were cultured with Con A [2.5 ug/ml] at $1\times10^6$ cells/ml in 75 $cm^2$ tissue culture flasks for 48 hours in a humidified 5% $CO_2$/95% air incubator at 37° C. Supernatants was collected at 24 and 48 hours after Con A activation and frozen at −70° C. after centrifugation. Interleukins was measured using solid phase ELISA assay. Anti-IL-2, anti-IL-10, or anti-IFN-γ [PharMingen, San Diego, Calif.] was incubated on polyvinyl plastic 96 well microtiter plates with 0.01M carbonate buffer (pH 9.6) overnight at 4° C. The plates were blocked with 3% BSA in phosphate buffered saline for 3 hours. 100 µl of supernatants was added at various dilutions that are titered to the linear portion of the absorbance/concentration curve in triplicate and incubated for 1 hour at room temperature. After the plates w as washed five times with phosphate buffered saline Tween (0.05%), 100 µl peroxidase conjugated interleukin monoclonal antibody (with a different epitopic determinant than the first antibody used to coat the polyvinyl plate) at a 1:1000 concentration was added for 60 minutes. Subsequently, the peroxidase substrate O-phenylenediamine dihydrochloride was added and the absorbance measured at 450 nm. Standard curves with various amounts of the different interleukins were generated. Statistical analysis w as performed using a one-tailed Student's t-test.

EXAMPLE 8

Orally Administered Murine Type I Interferons Suppress Clinical Disease, Inflammation and Inhibit Proliferative Responses to MBP.

One to ten units of orally administered type 1 IFN had an immunological effect but was not adequate to suppress clinical relapses. Therefore, two groups of six immunized SJL/J mice were fed mock IFN or 100 units murine natural IFN-α/β three times per week beginning on day 30, following recovery from the first attack. Group clinical scores after the initial attack were not significantly different among the different groups. Clinical relapses occurred approximately 40 days after inoculation. Clinical scores demonstrated significant differences in outcome in the mock IFN fed versus 100 units murine natural IFN-α/β fed animals [p<0.03, see FIG. 1]. Two major relapses occured in the mock IFN fed group over the course of seven weeks with a resultant increased neurological deficit. The oral murine natural IFN-α/β group underwent a delayed single attack without residual neurological deficit. Oral murine natural IFN-α/β blunted the severity and decreased the group score between the initial attack and relapse.

Con A activation of draining inguinal lymph node cells was inhibited in mock IFN fed compared to animals fed 100 units murine natural IFN-α/β [88,222 cpm±1,910 vs. 38,095 cpm±3,160]. Lymph node cells from mock IFN fed animals tested with MBP generated a robust proliferative response, but that response was profoundly inhibited in murine natural IFN-α/β fed animals [14,052 cpm±842 vs. 448 cpm±50].

To determine whether there was inhibition to another sensitized antigen, antigen-specific proliferation of draining inguinal lymph node to a second sensitized antigen was examined, Mycobacterium tuberculosus hominis [MT], a component of MSCH inoculum. Lymph node cells from mock IFN fed animals generated a robust proliferative response to MT but that response is profoundly decreased in 100 unit murine natural IFN-α/β fed animals [52,401 cpm±857 vs. 5,214 cpm±808].

Animals were also examined histologically 65 days following immunization. There were significantly less inflammatory foci in the IFN fed group [0.5±0.1] compared to the control mock IFN group [1.8±1.1] [p<0.05]. Thus, orally administered murine natural type I interferons can suppress clinical disease, decrease inflammation and inhibit proliferation to MBP and MT.

EXAMPLE 9

Suppression of Relapse by Oral IFN-α/β Correlates with Decreased IFN-γ Secretion The intensity of disease in EAE has been associated with IFN-γ secretion after Con A stimulation of spleen cells. Therefore pooled spleen cells were stimulated from both mock fed [n=5] or 100 units fed [n=5] murine IFN-α/β with Con A [2.5 µg/ml] at $1\times10^6$ cells/ml for two days and supernatants were assayed by solid phase ELISA [IL-2, IL-10, IFN-γ]. Oral IFN-α/β consistently decreased IFN-γ a mediator of inflammation [exp #1, mock spleen 2,500 ng/ml±300 vs 100 unit spleen *1,100 ng/ml+200; exp #2, mock spleen 2,180 ng/ml±100 unit spleen 247 vs *143 ng/ml±13, *p<0.001 compared to mock IFN control]. There was also a decrease in IL-2, a T cell growth factor and increased IL-10 production, although these changes did not attain statistical significance.

The present invention illustrates that orally administered type 1 interferons can modify the biological response in CR-EAE when administered after animals recover from the initial attack. When given at adequate dosages, orally administered type 1 interferons suppress clinical relapses, diminish inflammation and inhibit proliferation of activated cells from draining inguinal lymph nodes, the natural sites for high frequencies of activated T cells from subcutaneously administered antigens. Thus, type 1 interferons are active by the oral route with significant immunological effects in susceptible immune compartments. Oral IFN consistently decreased Con A induced IFN-γ secretion in spleen cells. Suppression of proliferation to MBP can occur even after a period of 6 weeks post-inoculation and 4 weeks after initial clinical attack. Thus, orally administered cytokines, lacking a protective matrix to prevent protein digestion in the oropharynx and the rest of the alimentary canal, are capable of inhibiting proliferation to previously sensitized antigens.

The blunting of an established and ongoing immune response is an important therapeutic issue. The administration of animal myelin antigens by the oral route can improve the clinical course of CR-EAE in rats and guinea pigs and decrease pathological sequellae to myelin antigens in CR-EAE. Oral administration of myelin proteins can decrease the severity of attacks in male DR2-MS patients and the frequency of MBP specific T cell lines in myelin treated individuals. However, in the human trials and animal experiments, there was only partial suppression of clinical or pathological disease suggesting that other orally administered immunoactive substances may be superior to myelin antigens.

The immunomodulatory mechanism of orally administered type 1 interferon is not known. Modulatory effects of Con A activated lymphocytes on the mitogen responses of normal responder cells can be abrogated by addition of anti-human leukocyte IFN serum in vitro; this may prevent the production of inhibitory factors induced by IFN-α, e.g. soluble immune response suppressor [SIRS] and macrophage derived suppressor factor [Mø-SF]. Peripheralized T cells may be required for interferon production after such mitogen stimulation. However, oral administration of low dose IFN-α in mice does not result in detectable levels of IFN-α in the blood in contrast to intraperitoneal administration, nor can its effect be blocked by circulating anti-IFN antibodies. The neutropenic effect of orally administered IFN can be transferred by injection of blood cells but not serum to recipient animals. Cytokine mRNA analysis of the CNS in EAE suggests that IL-2, IL-6 and IFN-γ are elevated in acute disease but during stabilization of symptoms these cytokines are decreased with increasing IL-10 levels which can regulate Th1 cells. Therefore type 1 IFN is an immunomodulatory molecule which induce suppressor factors, such as IL-10, inhibiting response to immunized antigens such as MBP and MT.

In summary, the oral administration of biological response modifiers such as type I interferons provides a potentially non-toxic, convenient and continuous means of inhibiting immune responsiveness. Biological response modifiers delivered by the oral route provide another means to treat autoimmune diseases.

EXAMPLE 10

Induction of Acute Experimental Autoimmune Encephalomyelitis.

EAE was induced in 8-10 week old female Lewis rats [Harlan Sprague Dawley, Indianapolis, Ind.], using an emulsion containing equal parts of myelin basic protein in PBS and complete Freund's adjuvant [CFA]; *Mycobacterium tuberculosus hominis* H37Ra [MT] [Difco Labs, Detroit, Mich.]. Lewis rats were immunized s.c. in a rear footpad with 0.1 ml emulsion containing 50 µg MBP and 500 µg MT in Freund's adjuvant. Initial clinical signs of disease were seen between days 9 and 11 postimmunization. Clinical severity of the initial attack was graded as follows by a blinded observer: 0=no disease; 1=flaccid tail; 2=slight hind limb weakness; 3=moderate hind limb weakness; 4=total hind limb weakness and incontinence. Average daily clinical score was calculated by determining the average score for each group on each day of attack. A experimental allergic encephalomyelitis cumulative clinical score was calculated that incorporated overall clinical severity, disease incidence and duration of clinical signs into one comparative index by summing all daily scores on all rats in a treatment group between onset and end of attack and dividing by the total number of rats within the treatment group. Statistical analysis was performed on combined data from at least two similar experiments.

EXAMPLE 11

Administration of IFN

Seven days preceding immunization [−7] and for 21 days thereafter [+14], rats were fed either mock IFN, 1,000, 3,000 or 5,000 units rat natural IFN-α/β [Cytimmune rat IFN α+β, $4.0 \times 10^5$ IRU/ml, Lee Biomolecular Research, Inc. San Diego, Calif.] or human recombinant IFN-α [hrIFN-α] [IFN-$\alpha_{II}$ $3.0 \times 10^6$ IU/ml, Schering Corp, Kenilworth, N.J.] using a syringe fitted with a 20 gauge ball point needle [Thomas Scientific, Swedesboro, N.J.] placed in the posterior oropharynx or injected subcutaneously with PBS placebo or 5,000 units hrIFN-α daily. Lyophilized IFN preparations were reconstituted with DPBS and diluted 1/600 to 1/3,000. The mock natural preparation was prepared identically to the rat natural IFN-α/β but is not induced with Newcastle virus.

Preparation of guinea pig myelin basic protein [GP-MBP], i.e., homogenization and delipidation, acid elution of MBP, lymph node cell and spleen preparation, in vitro T cell proliferation and cytokine analysis were performed as described above.

EXAMPLE 12

Histology

Following sacrifice, spinal cords were removed and immersion fixed in 10% neutral buffered formalin for a minimum of two weeks. After fixation, cords were sectioned in entirety in the horizontal plane at approximately 3 mm intervals and processed to paraffin. Paraffin blocks were sectioned at 6-8 microns, and step sections [n=5] were stained with hematoxylin and eosin and with Luxol-fast blue/PAS/hematoxylin, and examined by light microscopy. Cord sections were evaluated independently for foci of inflammation by a blinded observer, without knowledge of the treatment status of the animals prior to sacrifice. Spinal cord tissue was sampled in an identical fashion for each animal and numbers of inflammatory foci per section (>20 inflammatory cells) in the parenchyma were counted. Statistical analysis was performed using a two-tailed Student's t-test.

EXAMPLE 13

Figure 2:
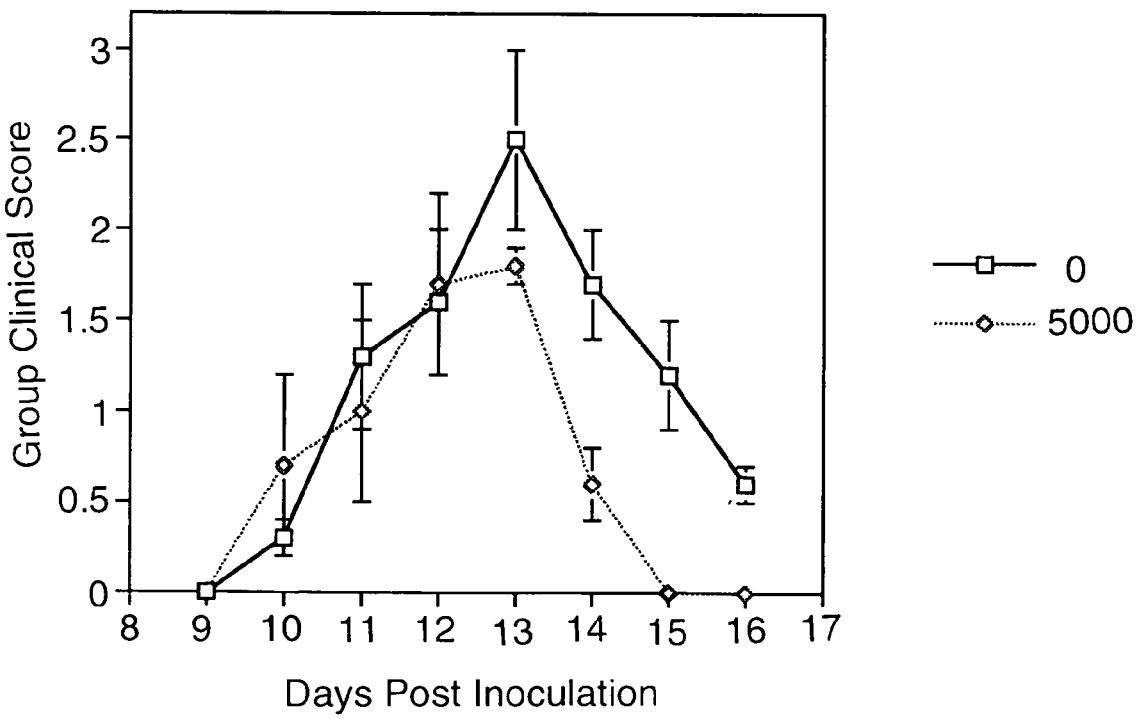
FIG. 2 shows that oral administration of 5,000 units rat IFN-α/β inhibits clinical disease in acute EAE. Four groups of 6 Lewis rat were fed mock IFN, 1,000, 3,000 or 5,000 units rat IFN-α/β for seven days preceding immunization [−7] and for 21 days thereafter [+14]. Results are expressed as average clinical score for each group on each day of disease post-innoculation±SEM. One of two representative experiments is shown. Data for 1,000 and 3,000 units are not shown. *p<0.02 between mock and 5,000 unit IFN-α/β fed animals.

Natural Rat Interferon Alpha/beta Modifies Clinical Disease, Inhibits Proliferative Response and Decreases Inflammation to GP-MBP Four groups of six 8-10 week old Lewis rats were immunized with equal parts MBP and CFA and subsequently had attacks beginning by day 9 and followed until day 16. Seven days preceding immunization [−7] and for 21 days thereafter [+14], each group of animals were fed either mock IFN, 1,000, 3,000, or 5,000 units rat type 1 IFN-α/β daily in 0.1 ml PBS. All animals were scored for clinical disease until day 16 after immunization. Results from blinded examination of daily group clinical scores demonstrated significant differences in clinical outcome in the mock fed versus 5,000 units IFN-α/β fed animals particularly at days 13-16 but not in the animals fed 1,000 or 3,000 units. Rats treated with 5,000 units rat natural IFN-α/β had peak disease that was less severe than in the mock group, and the 5,000 unit IFN-α/β treated group recovered more quickly and returned to baseline sooner than the mock treated group [FIG. 2, data not shown for 1,000 and 3,000 units]. The experimental allergic encephalomyelitis cumulative clinical score of the animals treated with 5,000 units rat natural IFN-α was significantly less than mock IFN fed controls [0.8±0.2, 5,000 unit fed vs 1.2±0.2, mock IFN fed, p<0.02]. Animals were also examined histologically 16 days following immunization. There were less inflammatory foci in the IFN-α/β treated [26±6] compared to the control mock interferon group [50±2] although this did not attain statistical significance due to the small number of spinal cords examined per group [n=3] [p<0.06].

Draining popliteal lymph node Con A proliferation was inhibited from 16,209±1,234 cpm from mock fed animals to 8,120±765 cpm in 5,000 unit IFN-α/β fed animals. Draining popliteal lymph node cells from mock and 5,000 unit treated animals were stimulated with ionomycin+PMA and demonstrated decreasing proliferation from mock [20,505 cpm±505] to 5,000 [6,111 cpm±636] unit treated animals. No consistent differences in MBP or MT proliferation between fed and mock fed animals was demonstrated in draining popliteal lymph node. There was also no inhibition in spleen or non-draining mesenteric lymph node to Con A or ionomycin/PMA in IFN treated animals.

Thus, species specific type I interferons inhibit the severity of acute clinical disease when given at adequate dosages. Inhibition of proliferation from orally administered IFN-α/β could be due to a direct action of IFN which enters the bloodstream through the gut or indirectly. The in vitro type I IFN treatment of draining popliteal lymph node and spleen cells was examined from immunized but mock treated animals demonstrates similar effects to in vivo treatment. There was no clear effect on Con A proliferation in draining popliteal lymph node or spleen cells exposed to IFN [1-100 units] in vitro, in contrast to in vivo IFN oral administration in which draining popliteal lymph node proliferation was decreased. Thus, an indirect effect of type 1 IFN may be mediated through the gut associated lymphoid tissue.

EXAMPLE 14

Figure 3:
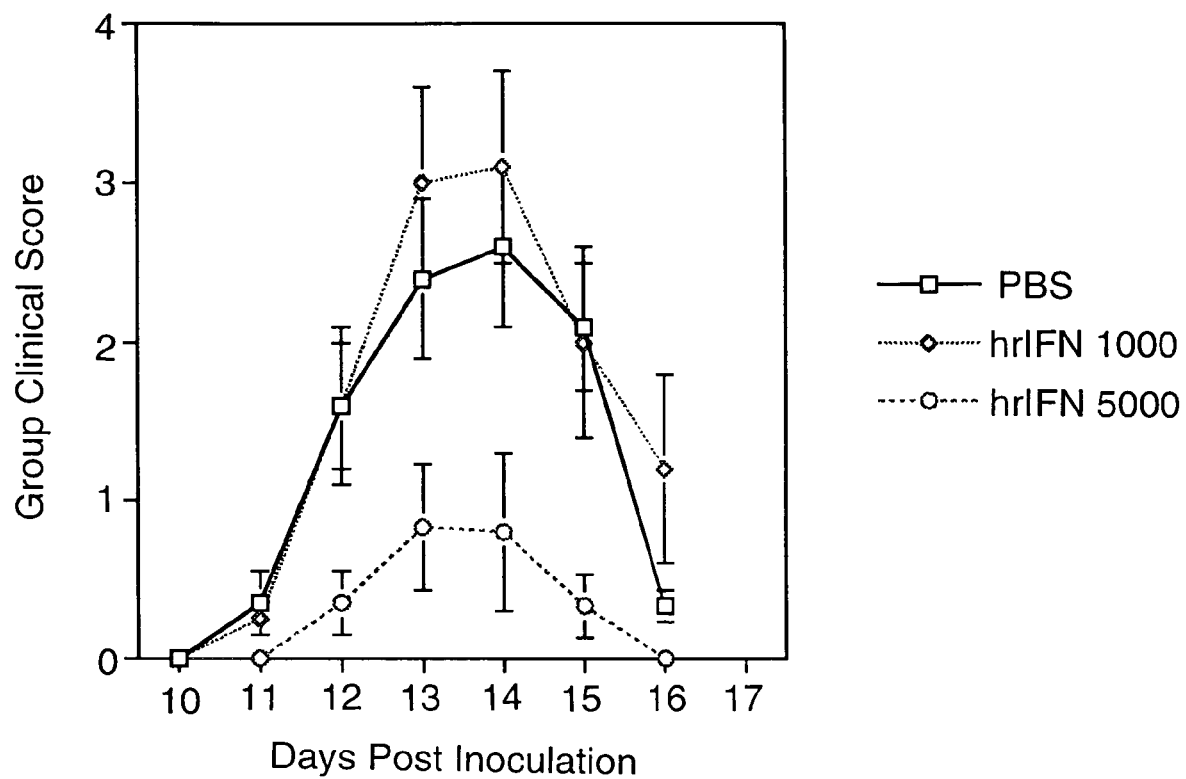
FIG. 3 shows that oral administration of hrIFN-α in rat acute EAE delays the onset, decreases the severity and speeds t h e recovery of clinical attacks. Three groups of seven Lewis rats were inoculated with MBP and CFA on day 0 and orally administered PBS, 1,000 units or 5,000 units hrIFN-α daily starting seven days preceding immunization [−7] and for 14 days thereafter [+14]. Values represent mexperimental allergic neuritis clinical scores for each group of 7 animals±SEM. One of two representative experiments are shown.
Figure 4:
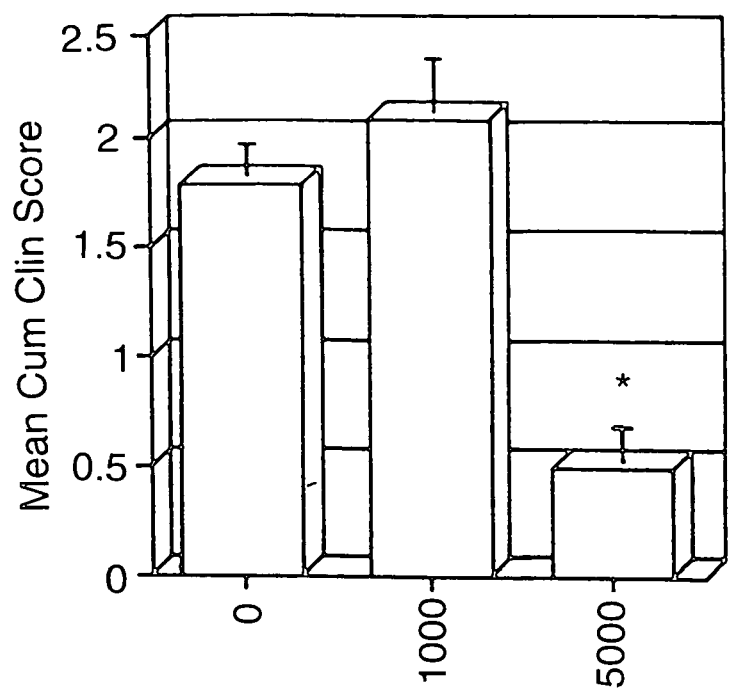
FIG. 4 shows that oral administration of hrIFN-α in rat acute EAE decreases the experimental allergic neuritis cumulative clinical severity of acute clinical attacks. Three groups of seven Lewis rats were treated as described in FIG. 3. Values represent experimental allergic neuritis cumulative clinical scores for each group of 7 animals from day 10 to 16 post-innoculation. *p<0.001, 5,000 units IFN-α vs. both 1,000 units IFN-α and PBS control.
Figure 5:
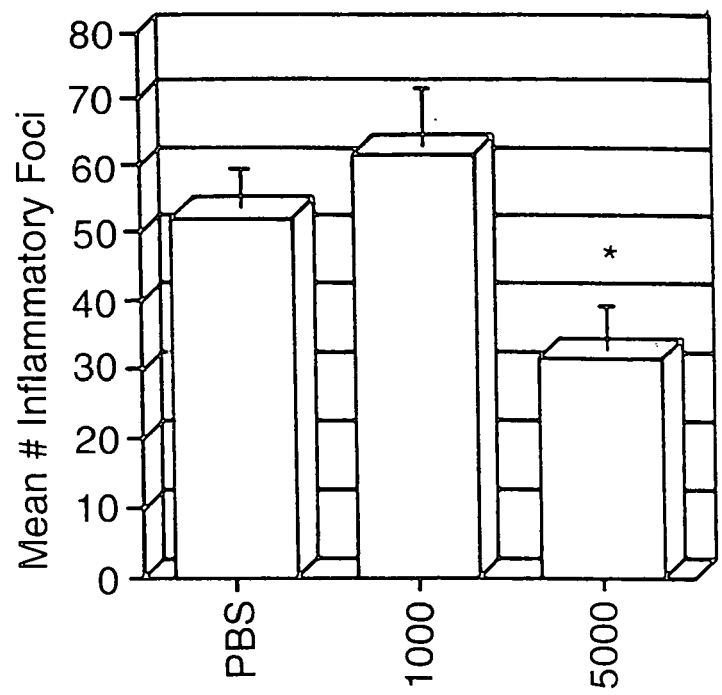
FIG. 5 shows that oral administration of 5,000 units hrIFN-α decreases the number of inflammatory foci in spinal cord compared to the control and 1,000 interferon group. Following sacrifice, spinal cords from animals in FIG. 3 were processed as described in methods. Results are expressed as # of inflammatory foci per cord±SEM. One of two representative experiments is shown. *$p<0.04$, 5,000 units IFN fed vs. 1,000 unit IFN fed or PBS control group.

Modification of Acute Rat EAE by Oral Administration of Human Recombinant Interferon Alpha Since human type 1 interferon can show cross-species activity in mice, guinea pigs, gnotobiotic calves, horses and pigs, and cats, recombinant human interferon [hrIFN-α], a uniform material that may provide more immunosuppression per unit of activity than natural preparations, was utilized. For seven days preceding immunization [−7] and for 21 days thereafter [+14], each group of animals was fed either PBS, 1,000 units or 5,000 units hrIFN-α daily. Three groups of seven 8-10 week old Lewis rats were immunized and subsequently had an attack beginning by day 10 and extending through day 16. All animals were scored for clinical disease until day 16 after immunization. As shown in FIG. 3, PBS and 1,000 unit hrIFN-α fed animals demonstrated severe acute attacks starting at day 10 and reaching peak intensity at day 14. Animals fed 5,000 units hrIFN-α showed delayed attack onset, decreased severity a t peak and earlier resolution of the attack. The experimental allergic encephalomyelitis cumulative clinical score of the animals treated with 5,000 units hrIFN-α was significantly less than either PBS control fed or 1,000 unit fed animals [FIG. 4]. Thus, orally administered hrIFN-α suppress the onset of clinical attacks of EAE in the Lewis rat when administered before inoculation. Following sacrifice 16 days post-immunization, animals were also examined histologically. There were significantly fewer inflammatory foci in 5,000 unit hrIFN-α fed group compared to the PBS control group or 1,000 unit hrIFN-α fed group [FIG. 5].

EXAMPLE 15

Figure 6:
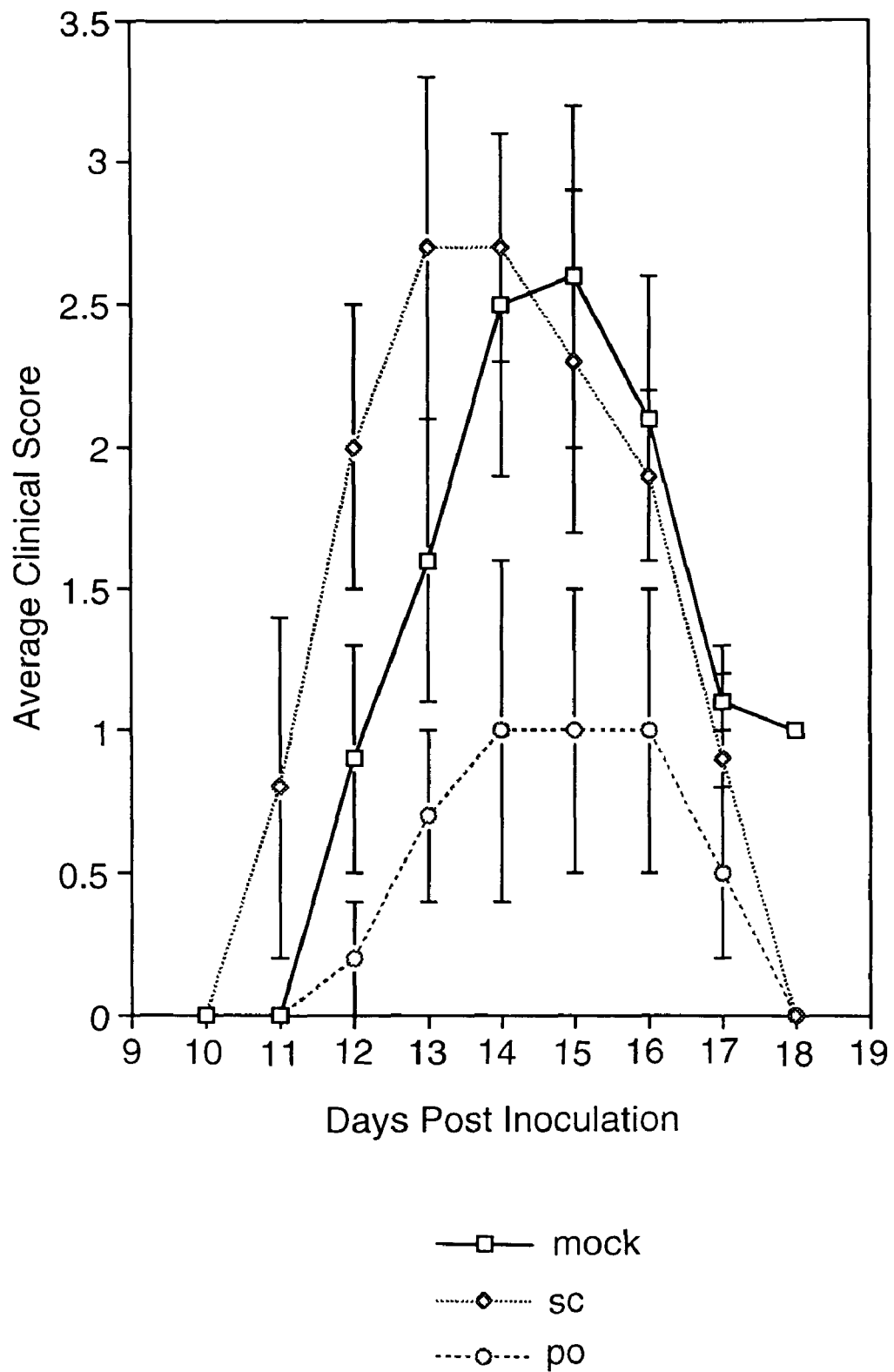
FIG. 6 shows that oral administration of 5,000 units hrIFN-α, and not subcutaneous, administration decreases the severity of clinical attacks. Three groups of 6 Lewis rats were inoculated with MBP and CFA on day 0 and untreated, fed 5,000, or injected s.c. with 5,000 units hrIFN-α daily starting seven days preceding immunization [−7] and for 21 days thereafter [+14]. Values represent experimental allergic neuritis daily clinical scores for each group of 6 animals±SEM. One of two representative experiments are shown.
Figure 7:
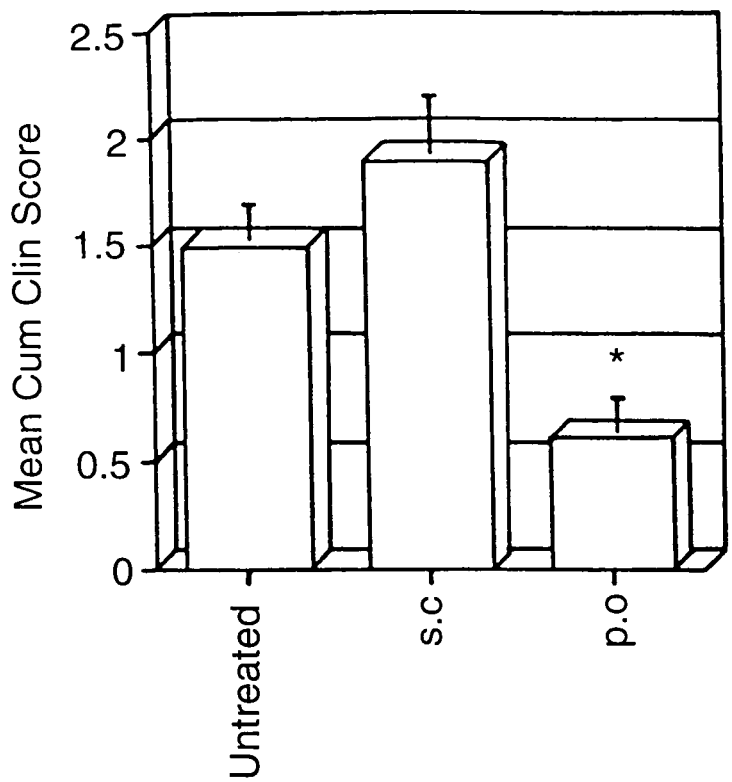
FIG. 7 shows that oral administration of hrIFN-α in rat acute EAE decreases the experimental allergic neuritis cumulative clinical severity of acute clinical attacks. Three groups of six Lewis rats were treated as described in FIG. 6. Values represent experimental allergic neuritis cumulative clinical scores for each group of 6 animals from day 10 to 16 post-inoculation. *$p<0.005$, fed animals vs. untreated/s.c. treated animals.
Figure 8:
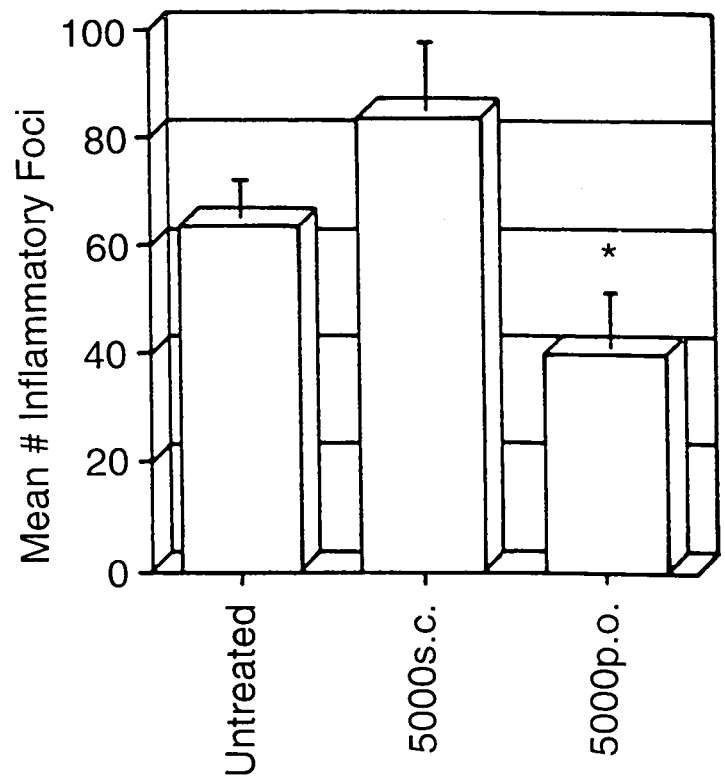
FIG. 8 shows that oral administration of 5,000 units hrIFN-α decreases the number of inflammatory foci in spinal cord compared to the control group. Following sacrifice, spinal cords from animals in FIG. 6 were processed as described above and evaluated independently for foci of inflammation by one observer, without knowledge of the treatment status. Results are expressed as # of inflammatory foci per cord±SEM. One of two representative experiments is shown. *$p<0.04$, 5,000 units IFN fed vs. 5,000 units s.c. treated.

Oral but not Equivalent Doses of Parenteral Administered Human Recombinant Interferon Alpha Modifies Clinical Disease Orally administered hrIFN-α modifies clinical disease and decrease inflammation in spinal cord. The relative efficacy of equivalent amounts of orally versus parenterally administered hrIFN-α was examined. Three groups of six Lewis rats were immunized and either untreated, fed 5,000 units hrIFN-α or injected with 5,000 units hrIFN-α s.c. for seven days preceding immunization [−7] and for 21 days thereafter [+14]. All animals were scored for clinical disease until day 18 after immunization. Rats treated with oral 5,000 units hrIFN-α had a less severe disease at peak of the disease and more rapid recovery compared to the untreated group [FIG. 6]. Indeed, the untreated and the s.c. treated groups had very similar clinical curve scores, suggesting that s.c. hrIFN-α had little or no effect on clinical disease. Experimental allergic encephalomyelitis cumulative clinical scores demonstrated significant differences in clinical outcome in the untreated/sc treated vs fed animals [FIG. 7]. There was no significant difference between untreated and s.c. treated animals. Eighteen days following immunization, animals were sacrificed and examined histologically. There were significantly fewer inflammatory foci in 5,000 unit fed compared to the 5,000 units s.c. treated group [FIG. 8].

PBS fed and PBS s.c. injected controls demonstrated similar findings. In this case four groups of six Lewis rats were either fed PBS, injected s.c. with PBS, fed 5,000 units hrIFN-α or injected with 5,000 units hrIFN-α s.c. for seven days preceding immunization [−7] and for 21 days thereafter [+14]. All animals were immunized on day 0. Animals were scored for clinical disease until day 16 after immunization and sacrificed. Experimental allergic encephalomyelitis cumulative clinical scores were significantly less in hrIFN-α fed animals [1.0±0.2] compared to PBS fed [2.5±0.4] [p<0.005]. There was no significant difference between mock s.c. [1.7±0.4] and 5,000 units hrIFN-α s.c. [2.1±0.4] animals even though s.c. treated animals did have higher experimental allergic encephalomyelitis cumulative clinical scores. Thus, s.c. administered hrIFN-α cannot modify the onset of acute clinical disease when given at clinically preventive oral dosages.

EXAMPLE 16

Orally Administered IFN-α Inhibits the Mitogen Induced Production of IFN-γ in Draining Popliteal Lymph Nodes The intensity of disease in EAE has been associated with IFN-γ secretion after Con A stimulation. Therefore, spleen and draining popliteal lymph node cells [day 18 post-immunization] from both mock fed or 5,000 units fed hrIFN-α rats were stimulated with Con A [2.5 µg/ml] for two days and supernatants were assayed by ELISA. The results in TABLE I show that oral hrIFN-α decreased IFN-γ, a mediator of inflammation, in draining popliteal lymph node but not in spleen.

TABLE I

Inhibition of clinical disease by oral IFN correlates with decreased IFN-γ secretion in draining popliteal lymph nodes

|  | LN mock | LN 5,000 | spleen mock | spleen 5,000 |
|---|---|---|---|---|
| IFN-γ [ng/ml] | 461 ± 60 | 96 ± 32* | 360 ± 75 | 310 ± 62 |

Spleen and draining popliteal lymph node cells [day 18] from mock IFN and 5,000 unit IFN fed immunized rats were cultured with Con A [2.5 µg/ml] at $1\times10^6$ cells/ml for 48 hours. Supernatants were collected at 48 hours after Con A activation and frozen at $-70°$ C. after centrifugation. IFN-γ was measured using solid phase ELISA assay. Results given are expressed in ng/ml. Combined data from two experiments are shown. LN 5,000 compared to LN mock *p<0.05.

Orally administered type 1 interferons, as opposed to identical s.c. doses, are disclosed by the present invention as modifiers of biological response to MBP in acute EAE in Lewis rats when they are administered before sensitization and clinical attack. Orally administered type 1 interferons partially modify clinical attacks, decrease the number of inflammatory foci in spinal cord, decrease non-specific proliferation by Con A and ionomycin/PMA and decrease the production of IFN-γ in draining popliteal lymph nodes. This suggests that IFN-α is more active by the oral route, and has definable immunological effects, and confirms that specific cytokines are capable of inhibiting clinical disease when given via the GI tract.

Surprisingly, both human recombinant IFN-α and species-specific rat natural IFN worked in present invention. Natural IFNs are a mixture of 14 separate subspecies including the IFN-$α_{II}$ subtype which may be only a small component of the natural type. Human IFN shows some cross species activity, however, the exclusive use of the IFN $α_{II}$ subtype may provide a relative greater amount by inhibitory activity/total units of activity of the most important component for immunosuppression in the rat.

Antiproliferative effects of orally administered IFN were greater in draining popliteal lymph node than in non-draining popliteal lymph nodes. The oral administration of IFN-α also inhibited the production of IFN-α in draining popliteal lymph nodes. Draining popliteal lymph node are the natural draining areas for subcutaneously administered antigens and therefore presumably the reservoir of high frequencies of sensitized MBP-specific T cells. Orally administered cytokines may preferentially effect proliferation and cytokine production at sites of immune activation compared to systemic administration. Inhibition of IFN-γ secretion in an activated regional immune compartment by IFN-α may cause decreased inflammatory effect of MBP-specific cells in the CNS.

Oral IFN-α was effective in inhibiting EAE compared to identical s.c. doses. In vitro IFN did not inhibit Con A proliferation in pop LN in contrast to in vivo p.o. administration. Thus, the route of administration is critical and may determine the immunological mechanism for IFN. Proteins which might not survive transit through the alimentary canal may still exhibit immunoinhibitory activity via the gut associated lymphoid tissue [GALT] in the oropharynx. Therefore oral administration provides an alternative drug delivery system for therapeutic cytokines in the treatment of autoimmune diseases by the generation of immunoregulatory cells via the gut immune system.

The immunomodulatory mechanism of orally administered type 1 interferon is not known. Modulatory effects of Con A activated lymphocytes on the mitogen responses of normal responder cells can be abrogated by addition of anti-human leukocyte IFN serum in vitro which may modify the production of inhibitory factors induced by IFN-α, e.g. soluble immune response suppressor [SIRS] and macrophage derived suppressor factor [Mø-SF]. Peripheralized T cells may be required for interferon production after such mitogen stimulation. However, oral administration of low dose IFN in mice does not result in detectable levels of IFN in the blood in contrast to intraperitoneal administration, nor can its effect be blocked by circulating anti-IFN antibodies. The neutropenic effect of orally administered IFN can be transferred by injection of blood cells but not serum to recipient animals. Similarly, cells can be induced in Peyer's patch after oral administration of antigen in mice that decrease humoral response in vitro. Therefore, type 1 IFN may be an immunomodulatory molecule produced by activated T and other immune cells which induce suppressor factors, such as SIRS and Mø-SF, inhibiting response to immunized antigens such as MBP.

The present invention demonstrates that oral IFN-α therapy is relevant for relapsing-remitting multiple sclerosis and other chronic non-neurological autoimmune diseases since orally administered IFN-α appears to be more effective than equivalent doses of parenteral IFN-α. Thus, the oral administration of cytokine biological response modifiers such as IFN-α provides an effective means of modifying clinical attacks to an autoantigen when administered before sensitization. The oral route is a convenient drug delivery system that allows the use of significantly lower doses of cytokines, minimizing side effects and enhancing efficacy.

EXAMPLE 17

Immunization

Female Lewis rats (Harlan), 150-170 g in weight, were immunized with 20 mg (wet weight) peripheral nerve myelin emulsified in an equal volume of complete Freund's adjuvant (CFA) which contained 10 mg M. tuberculosis per ml Freund's. The immunogen was injected in 200 µl into the footpad of the right hindleg. Peripheral nerve myelin was isolated from bovine spinal roots (Pel-Freeze, Tex.) according to the method of Norton, Methods Enzymol., 31 (part A), 435, 1975.

EXAMPLE 18

Interferon Administration

Starting seven days preceding immunization until sacrifice at 20 days after immunization, rats were fed either mock-IFN or 5000 U rat natural IFN-α/β (Cytimmune rat IFN-α/β 1.5× $10^6$ U/ml, Lee Biomolecular Research Inc, San Diego, Calif.). Lyophilized IFN was reconstituted with sterile water, diluted in phosphate buffered saline (PBS) and administered in a 0.1 ml daily dose using a syringe fitted with a 20 gauge ball point needle (Thomas Scientific, Swedesboro, N.J.) placed in the posterior oropharynx.

EXAMPLE 19

Clinical Assessment

The rats were weighed daily starting at day 7 after immunization and evaluated clinically using the following scale: 0, normal; 1, limp tail; 2, abnormal gait; 3, mild paraparesis; 4, severe paraparesis; 5, paraplegia; 6, paraplegia with forelimb involvement; 7, paraplegia with forelimb involvement and respiratory distress; 8, moribund or dead as described by Hahn et al., *Acta Neuropathol.* 82:60-65 (1991). Weight loss was calculated for each animal as the difference between weight at time of sacrifice and maximum weight and expressed as a percentage of the maximum weight.

EXAMPLE 20

Proliferation Assays

At sacrifice on day 20 after immunization, draining popliteal lymph nodes and spleen were removed. Single cell suspensions were made by passage through 90 μm stainless wire meshes. Red cell lysis was performed in spleen cell suspensions by adding 2 ml of ACK solution to the pellet. Cells from spleens and draining lymph nodes were pooled for each treatment group for in vitro culture. Whole spleen or lymph node populations were incubated at $2\times10^5$ cells/ml with *M. tuberculosis* at 10 μg/ml, SP26 at 1 μg/ml [SP26 is a neuritogenic peptide of 26 aminoacids (Rostami et al., *J. Neuroimmunol.*, 30:145-151 (1990) synthesized in the Department of Analytical Chemistry at the University of Texas], Concanavalin A at 2.5 μg/ml (Sigma Chemical Co., St. Louis, Mo.) in RPMI (Gibco, Grand Island, N.Y.), ionomycin at 100 ng/ml (Calbiochem, La Jolla, Calif.) in combination with myristic acid palmityl ester (PMA) at 1 ng/ml (Sigma Chemical Co., St. Louis, Mo.) supplemented with 10% fetal calf serum (FCS; Whittaker Bioproducts, Walkersville, Md.), 1 mM sodium pyruvate (Gibco, Grand Island, N.Y.), 2 mM glutamine (Gibco), 100 units Penicillin/Streptomycin, and 50 μM 2-mercaptoethanol. The plates were incubated at 5% $CO_2$ and humidified at 37° C. for 4 days. At that time, the cells were pulsed with 2 μCi of tritiated (3H) dTd and harvested 18 hours later on an automated harvester. (3H) dTd uptake was measured in a Beckman liquid scintillation counter. Cultures were run in triplicate and the results expressed as ΔACPM.

EXAMPLE 21

Cytokine Analysis

Draining pooled popliteal lymph node and pooled spleen cells from mock and 5000 unit rat IFN treated experimental allergic neuritis animals were cultured with Con A (2.5 μg/ml), *M. tuberculosis* (10 μg/ml) or SP26 (1 μg/ml) at $1\times10^6$ cells/ml in 75 $cm^2$ tissue culture flasks for 48 hours in a humidified 5% $CO_2$/95% air incubator at 37° C. Supernatants were collected after centrifugation and frozen at −70° C. IFN-γ was measured using a solid phase ELISA assay. Anti-IFN-γ (Pharmingen, San Diego, Calif.) was incubated on polyvinyl plastic 96 well microtiter plates with 0.01M carbonate buffer (pH 9.6) overnight at 4° C. The plates were blocked with 3% bovine serum albumin (BSA) in PBS for 3 hours. One hundred μl of supernatants were added at various dilutions titered to the linear portion of the absorbance/concentration curve in triplicate and incubated for 1 hour at room temperature. After the plate was washed 5 times with PBS Tween (0.05%), 100 μl peroxidase conjugated IFN-γ monoclonal antibody (with a different epitopic determinant than the first antibody used to coat the polyvinyl plate) at a 1:1000 concentration was added for 60 minutes. Subsequently, the peroxidase substrate O-phenylenediamine dihydrochloride was added, and the absorbance measured at 450 nm. Standard curves with various amounts of IFN-γ were generated.

EXAMPLE 22

Histology

Rats were sacrificed by perfusion with saline under pentobarbital anesthesia on day 20 after immunization. The cauda equina was removed and divided. The distal portion was fixed in 2.5% paraformaldehyde/2.5% glutaraldehyde in PBS for 4-6 hours, osmicated overnight in 2% osmium tetroxide, dehydrated and embedded in Epon. Four to five blocks of the lower lumbosacral roots were prepared from each animal. Representative 0.5 micron sections of each block were stained with toluidine blue.

Histological assessment of demyelination and inflammation in each root was performed using the following scale (Hahn et al, 1991): demyelination 1+=a few demyelinated axons perivenular or scattered; 2+=many foci of perivenular demyelination; 3+=extensive demyelination perivenular and confluent; inflammation 1+=a few scattered mononuclear inflammatory cells often subperineurial; 2+=perivenular cuffing with mononuclear inflammatory cells; 3+=extensive multifocal perivenular cuffing and widespread endoneurial inflammation. Scores were calculated per animal by dividing the total number for demyelination and inflammation over the number of nerve roots in the sections. Slides were read by an investigator (MP) who was unaware of the immunization or treatment protocol pertaining to the specimens.

The proximal portion of the cauda equina (±2 cm) was snap-frozen in methylbutane cooled in liquid nitrogen and stored at −70° C. Eight micron cross-sections were cut on a cryostat, fixed in ice cold ether and used for immunocytochemistry.

EXAMPLE 23

Immunocytochemistry

Immunocytochemistry was performed using the following antibodies: ED1 1:1000 (macrophages), W3/13 (lymphocytes; Harlan Bioproducts for Science, IN), CD11b/c 1:100 (CR3 on macrophages, granulocytes, dendritic cells; Pharmingen, Calif.), IFN-γ 1:10 (Genzyme, MA). Eight micron frozen sections were blocked in normal rabbit serum for 30 minutes, then incubated with the primary antibody for 1 hour, washed with PBS, incubated with biotinylated secondary antibody for 1 hour, washed in PBS, incubated with ABC peroxidase (VECTASTAIN™) for 45 minutes, washed and developed with diaminobenzidine and hydrogenperoxide.

Blocking with 0.01% hydrogenperoxide preceded incubation with primary antibodies to IFN-γ. The intensity and distribution of staining in nerve roots was scored as 1+, mild; 2+, moderate and 3+, severe.

EXAMPLE 24

Clinical Symptoms

Figure 9A:
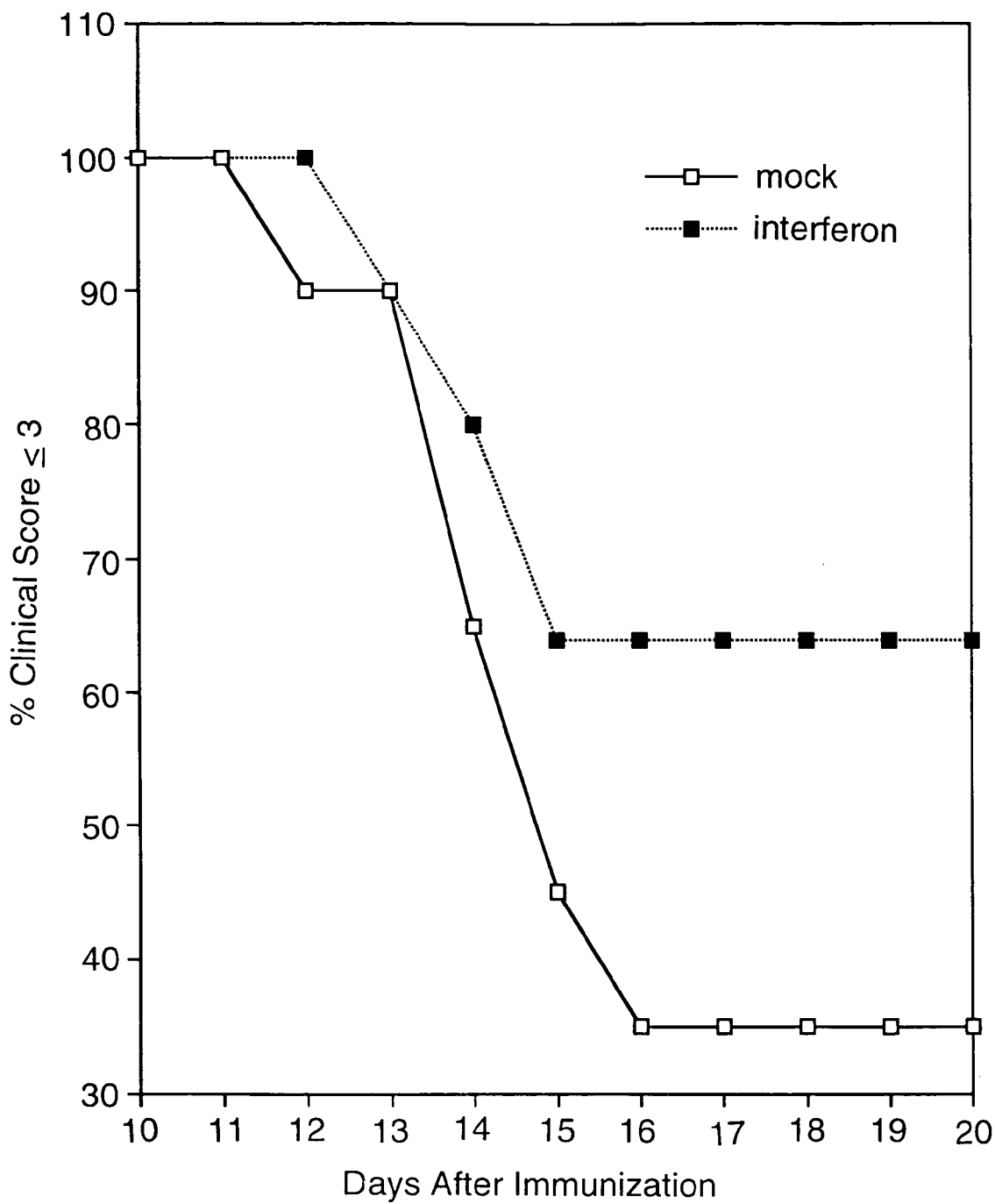
FIGS. 9A and 9B demonstrates that orally administered rat interferon-α/β reduces clinical disease in rats with experimental allergic neuritis. Lewis rats were fed either 5000 units IFN-α/β (interferon) or mock-IFN (mock) starting 7 days prior to immunization with bovine peripheral nerve myelin. Clinical score was significantly higher in the mock-IFN rats (n=11) than the IFN-α/β rats (n=11). More rats in the mock-IFN fed group than the IFN-α/β fed group reached a clinical score of 4 or higher (mock-IFN 7 of 11 vs IFN-α/β 4 of 11 rats) (FIG. 9A) and lost 25% or more of their body weight (mock-IFN 4 of 11 vs IFN-α/β 2 of 11 rats) (FIG. 9B).
Figure 9B:
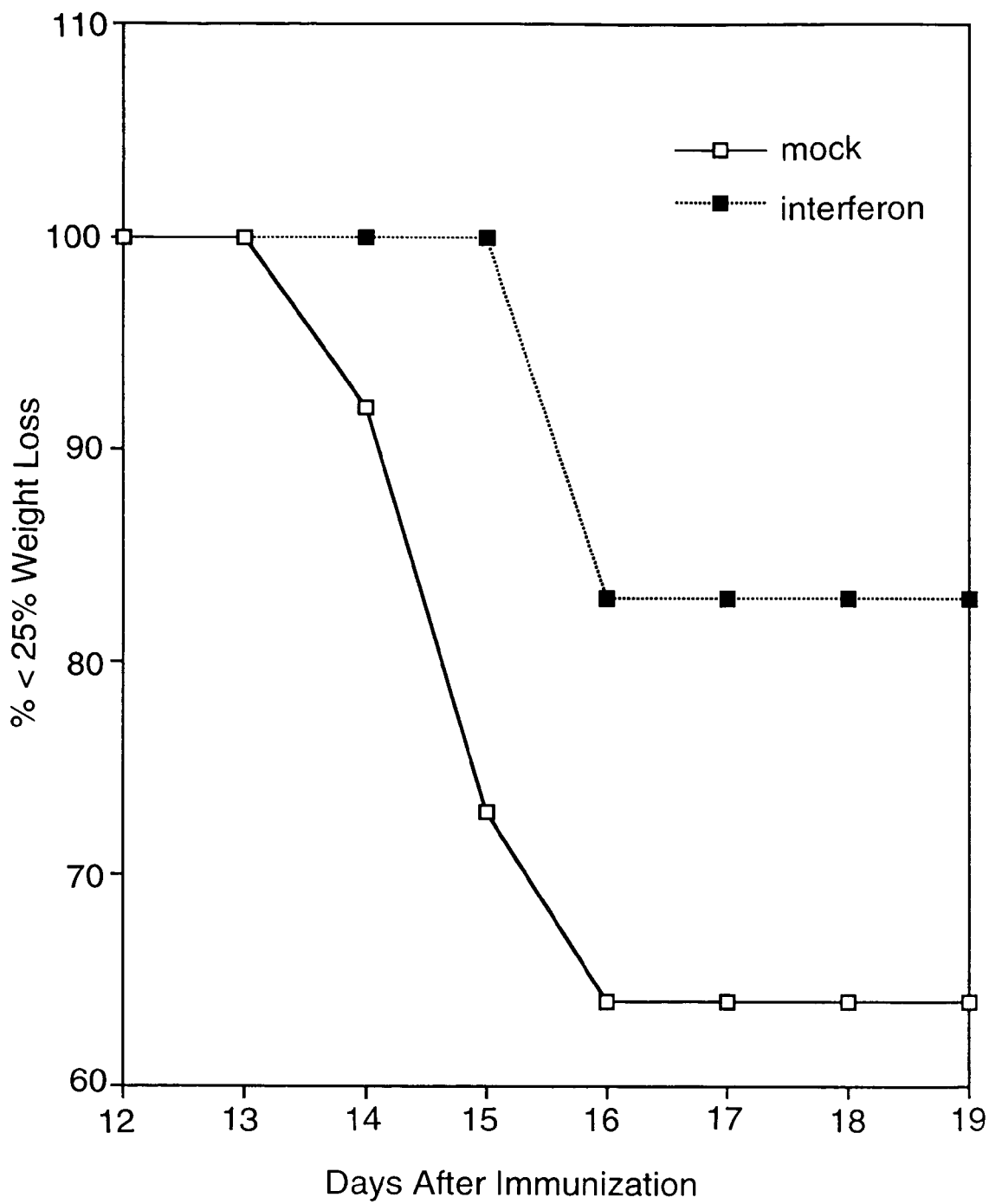
Figure 10A:
FIG. 10 demonstrates that orally administered rat interferon-α/β reduced inflammation and IFN-γ production in experimental allergic neuritis. Lewis rats were fed either 5000 units IFN-α/β or mock-IFN starting 7 days prior to immunization with bovine peripheral nerve myelin until the time of sarifice. Immunocytochemistry of lumbosacral nerve roots using ED1 antibody (1:1000) and IFN-γ antibody (1:10) on day 13 after immunization at the onset of clinical disease showed less ED1 positive macrophages (FIGS. 10A, 2B) in IFN-α/β fed rats compared to mock-IFN fed rats (FIGS. 10D, 10E). Concomitantly with reduced ED1 positive macrophages there was less IFN-γ expression in IFN-α/β fed rats (FIG. 10C) compared to mock-IFN fed rats.
(FIG. 10F) Bar=20 microns.
Figure 10B:
Figure 10C:
Figure 10D:
Figure 10E:
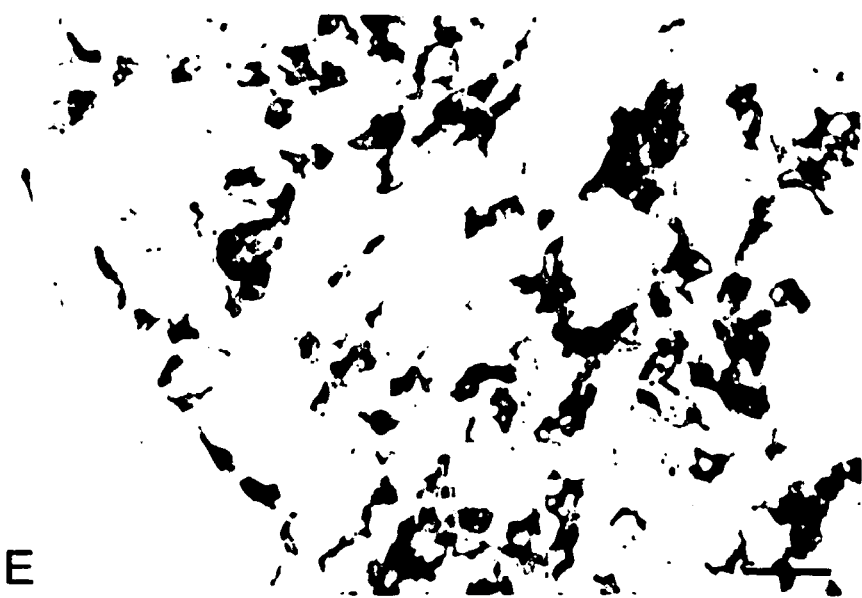
Figure 10F:
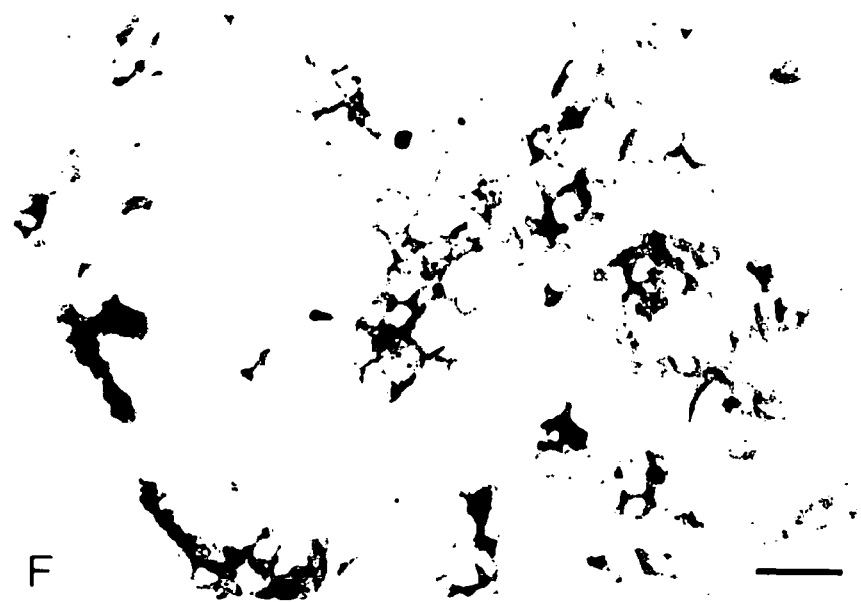

Rats started losing weight at day 10 after immunization and the first neurological symptoms appeared on day 12 while recovery started at day 16 or later. Eleven of 22 rats (50%) developed severe experimental allergic neuritis with a clinical score of 4 (severe paraparesis) or more and 2 out of 11 mock-IFN fed animals died on day 14 and 15 after immunization, while none of the IFN-α/β fed animals died. The clinical score in the mock-IFN fed rats (n=11, score 4.1±2.4; experimental allergic neuritis±SD) was significantly higher than in the IFN-α/β fed rats (n=11, score 3.3±1.4; p<0.03, Wilcoxon rank test). More rats in the mock-IFN fed group developed a clinical score of 4 or greater (FIG. 9A). Similarly more mock-IFN fed animals lost more than 25% of their body weight than IFN-α/β fed animals (FIG. 9B).

EXAMPLE 25

Cell Proliferation and Cytokines

Spleen cell proliferation to Con A from IFN-α/β fed animals was decreased compared to mock-IFN fed animals. (spleen: mock-IFN 118,114±5,194 vs rat IFN-α/β 835±94, mean±SEM, p<0.006, t-test). IFN-γ production after stimulation with SP26 by lymph node and spleen cells from mock-IFN fed rats was much higher than IFN-γ production by lymph node and spleen cells from IFN-α/β fed rats as measured by ELISA but the diffrence did not reach statistical significance (lymph node: 18.9±2.4 ng/ml vs 11.9±3.8 ng/ml; spleen: 11.9±0.4 ng/ml vs 6.3±1.8 ng/ml, mean±SEM, mock-IFN fed vs rat IFN-α/β fed, p<0.08). No difference in IFN-γ production was observed after stimulation with Con A or $M. tuberculosis$.

EXAMPLE 26

Histology

Histology of Epon-embedded sections showed demyelination to be significantly less severe in rat IFN-α/β fed rats (score 0.88±0.11, mean±SD) compared to mock-IFN fed rats (score 1.1±0.26; p<0.05, t-test) but inflammation was not significantly different in both groups of animals (score 1.0±0.2 vs 1.18±0.24).

Immunocytochemistry with CD11bc antibody showed large numbers of inflammatory cells both perivascular and diffusely infiltrating nerve roots of the cauda equina in both rat IFN-α/β fed and mock-IFN fed rats when sacrificed at day 20. The majority of these cells were phagocytic ED1 positive macrophages and no significant differences were observed between rat IFN-α/β fed rats and mock-IFN fed animals in the extent of inflammation.

A group of rats treated with either rat IFN-α/β (n=3) or mock-IFN (n=3) were sacrificed early in the course of the disease a t day 13 after immunization. Immunocytochemistry was performed to evaluate IFN-γ production in situ, which is only seen up until day 14 in experimental allergic neuritis, as well as inflammation. Infiltration by ED1 positive macrophages and W3/13 positive lymphocytes was much less severe in IFN-α/β fed rats than in mock IFN fed controls. IFN-γ staining was present in areas of dense inflammation on the surface of inflammatory cells. FIG. 10 shows that IFN-γ staining was markedly reduced in IFN-α/β fed rats concomitantly with less extensive inflammation.

Administration of oral species-specific IFN-α/β compared to mock-IFN reduced the severity of experimental allergic neuritis, causing a significant decrease in clinical disease score and less weight loss. Histological data, collected at day 20 after immunization, when recovery had started, showed less demyelination in the IFN-α/β treated group without altering the extent of inflammation. At day 13 after immunization, in situ IFN-γ production was reduced together with inflammation as evaluated by immunocytochemistry. Proliferation studies of draining lymph node and spleen cells showed reduced proliferation to Con A in IFN-α/β fed experimental allergic neuritis rats compared to mock-IFN fed controls. Cytokine analysis revealed reduced IFN-γ production after stimulation with SP26, a peripheral nerve myelin antigen capable of inducing experimental allergic neuritis. In combination, the present invention demonstrates that oral administration of IFN-α/β reduces the severity of experimental allergic neuritis by a reduction in IFN-γ production. Thus, the present invention shows an immunomodulatory effect of oral IFN-α/β on the host immune system.

The mechanism by which oral IFN-α/β acts on the immune system is unknown but may include effects on Peyer's patches in the gut-associated lymphoid tissue (GALT) where regulatory cells can be generated. IFN-α may induce immunoregulatory factors derived from CD8+ T cells that are responsible for disease modification. The reduced IFN-γ production associated with oral IFN-α/β administration suggests a possible functional inhibition of systemic Th1-like T helper cells found in EAE that produce IFN-γ. This results in a diminution of T cell encephalitogenicity of actively or passively induced disease.

Parenteral IFN-γ administration has been shown to augment both myelin-induced and T-cell mediated experimental allergic neuritis with increased clinical signs and histological abnormalities and enhanced oxidative burst by macrophages, while the opposite effect was obtained by parenteral administration of anti-IFN-γ antibody. IFN-γ also induces MHC class I and II expression on Schwann cells in vitro. IFN-γ, an inflammatory cytokine released by Th1 CD4+ T-cells, can upregulate MHC Class II expression on macrophages and endothelial cells and activate macrophages that play an important role in myelin phagocytosis. Reduced IFN-γ expression and reduced inflammation was seen at the onset of clinical disease in IFN-α/β fed animals. Histological evaluation at the end of the disease process, when recovery had started, showed reduced demyelination but not inflammation in IFN-α/β fed animals. Decreased IFN-γ and inflammation in early stages and diminished demyelination at later stages of disease suggest a critical role for IFN-γ in the pathogenesis of experimental allergic neuritis. The inability to decrease inflammation in later stages of disease may be due to partial suppression of IFN-γ production, the influence of other cytokines and inflammatory mediators and the induction of rather severe experimental allergic neuritis.

In summary, oral interferon is a biological response modifier effective in modifying disease in another experimental autoimmune disease, experimental allergic neuritis. The results of the present invention in experimental allergic neuritis showing reduced disease in rats fed IFN-α/β illustrate that oral IFN-α/β administration would be useful in the treatment of human immune-mediated neuropathies as Guillain-Barré syndrome or chronic inflammatory demyelinating polyradiculoneuropathy (CIDP).

The present invention demonstrated that murine species-specific (mIFN-α) and hrIFN-α delivered to the stomach and small intestine of mice suppressed clinical relapse in chronic relapsing experimental autoimmune encephalomyelitis (CR-EAE), decreased inflammation and suppressed the adoptive transfer of EAE. The optimal clinically effective fed dose of IFN-α for suppression of EAE was 10 times less than the optimal, but clinically less effective, subcutaneous dose. Mice fed type I IFNs showed decreased mitogen and antigen-specific proliferative responses and decreased IFN-γ and IL-2 secretion ex vivo. Therefore systemic effects can be achieved with IFN-α administered directly to the upper gastrointestinal tract in experimental models of autoimmune disease. The use of parenterally administered type I IFNs is limited by clinical and chemical toxicities including the generation of IL-6, a potential polyclonal B cell activator. Furthermore, antibodies that abrogate IFN activity develop in a proportion of IFN-$β_{1b}$ treated patients, correlating with the loss of clinical benefit. Since the oral route of IFN administration produce systemic immunomodulation, whether ingested IFN-α was non-toxic, modulated proliferation or cytokine secretion, and had biological effects on a surrogate marker of disease activity in MS, serum sICAM-1, in humans was also determined.

Normal healthy controls (three different volunteers a t each dose of 300, 1,000, 3,000, 10,000, 30,000 or 100,000 units hrIFN-α [hrIFN-α Roche Pharmaceuticals], total=18) were assessed for baseline hematologic and chemical profile and urinalysis, and for immunologic function. They were then treated for two weeks b y ingesting hrIFN-α three times per week and reassessed for toxicity and immune function. Estimated dose equivalency of ingested IFN-α in man of 6-300 units was based on effective anti-viral dosages of human natural IFN-α in animals to be 0.1-5 units/lb, and by a direct extrapolation on a unit/kg basis of the most effective dose of mIFN-α in murine EAE of 10 units/20 mg mouse (=30,000 units/60 kg human). This provided the dose approximations for this study in normal volunteers. Also included was a 100,000 unit dose to insure a complete dose-response evaluation. Peripheral mononuclear cells (PMNC) were obtained by venipuncture at pretreatment and after two weeks of three per week (Monday, Wednesday, Friday) hrIFN-α treatments, and ex vivo proliferation responses and interleukin secretion measured.

Ingested hrIFN-α was not toxic at any dose used as measured by clinical survey (NCI toxicity scale), routine blood chemistries and urinalysis (data not shown). However there was a significant decrease in CD3-mediated IFN-γ secretion in normal volunteers ingesting 30,000 units hrIFN-α after treatment (FIG. 11, $p<0.05$ by paired t test), but not after 300, 1,000, 3,000 10,000 or 100,000 units. There were no other statistically significant alterations of CD3, Con A or ionomycin+PMA proliferation or secretion of IL-2, IL-4, IL-6, IL-10, TGF-β or TNF-α at any dose studied. Phenotypic analysis of human T cells was performed b y means of direct immunofluorescence with fluorescein-conjugated monoclonal antibodies examining CD3, CD4, CD8, CD14, CD19, CD56+/CD3-, CD3/CD4, CD8/CD3, Ia/CD3+, $Ta_1$, CD4/2H4, CD4/4B4, CD8/2H4, CD8/4B4 at a dilution of 1/20 (Becton-Dickinson, San Diego, Calif.). Background fluorescent reactivity was determined using isotype control FITC-conjugated monoclonal antibodies. Flow cytometric analysis was performed using an Epics C flow cytometer (Coulter Electronics, Hialeah, Fla.). Mean fluorescence intensity and percent positive cells were measured. Single batches of directly labeled monoclonal antibody were used.

Assay of mixed lymphocyte cultures was performed according to the method of R. H. Kerman, et al., *Transplantation* 30: 450 (1980). Briefly, mixed lymphocyte cultures assays (MLC) were performed using PMNC from patient-responders and stimulators from a pool of three unrelated normal-donors. PMNC were isolated from heparinized venous blood on Ficoll-Hypaque gradients and washed three times in Hanks' balanced salt solution (HBSS, Gibco). Viable PMNC were counted on hemacytometer by trypan blue exclusion and adjusted to the appropriate concentration in complete medium (RPMI-1640, Gibco; supplemented with 2 mM Hepes buffer, Sigma; 100 units penicillin, 100 μg streptomycin/ml, Gibco; 501g gentamycin/ml, Microbiological Assoc.; 200 mM L-glutamine, Gibco; $5\times10^{-5}$ M 2-mercaptoethanol, Sigma; and 15% heat-activated pooled human AB serum, Microbiological Assoc.). The MLC reaction consisted of $1\times10^5$ each of responding and irradiated stimulator PMNC (stimulators were irradiated with 3,000 rads at 500 rads/min from a $^{137}Cs$ source, J. L. Shepard and Assoc, Glendale, Calif.) in triplicates wells of round-bottomed Linbro microtiter plates. Cultures were incubated at 37° C. in a 95% humidity, 5% $CO_2$ atmosphere. MLCs were pulsed on day 6 of culture with 1 μCi $^3H$-thymidine (specific activity, 5.0 c/mM; ICN) added to each well and harvested 18 hr later with a multiple automatic sample harvester unit. The filter strips were dried and counted in Packard-Beta Max system and data calculated as mean cpm for each triplicate sample. Stimulation index (S.I.) was calculated according to the formula: panel MLC SI=cpm from MLC of patient×pooled stimulators/cpm from control MLC of patient×irradiated autologous patient PMNC. The mixed lymphocyte cultures (MLC) showed no significant changes in this population with treatment.

Figure 12:
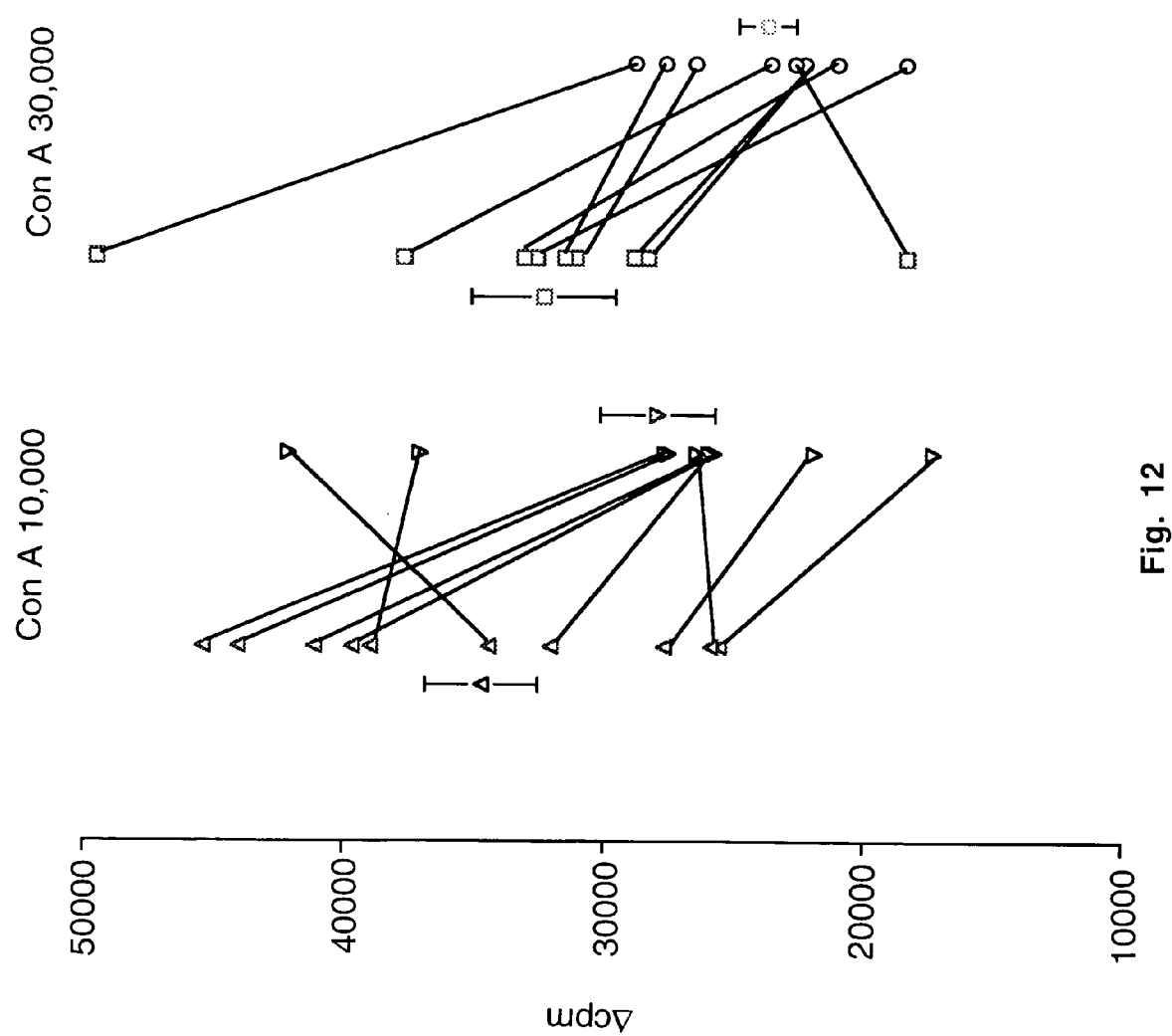
FIG. 12 shows subjects with early relapsing-remitting multiple sclerosis ingesting IFN-α demonstrate decreased Con A-mediated proliferation. Recruitment of the subjects with clinically stable relapsing-remitting multiple sclerosis was from patients in the MS Research Group Clinic of the University of Texas-Houston at Hermann Hospital. The diagnosis of relapsing-remitting multiple sclerosis was determined using defined criteria. Subjects with relapsing-remitting multiple sclerosis were administered IFN for two weeks at each dose with at least two weeks washout without IFN between the first dosing cycle (10,000 units), the second dosing cycle (30,000 units) and the third dosing cycle (100,000 units. Drug administration and proliferation assays were performed as outlined in FIG. 11. PMNC were obtained by venipuncture from stable relapsing-remitting multiple sclerosis subjects at pretreatment and one hour after the last of a two week treatment cycle (n=10 at 10,000 [pre($\Delta$), post($\nabla$)], n=9 at 30,000 (pre($\square$), post($\bigcirc$)] and n=8 at 100,000 units [pre($\bullet$)), post($\bullet$)]) as described above. Two patients discontinued treatment; one patient became pregnant after the first dosing cycle and another had a mild sensory attack of MS after the second dosing cycle. PMNC were examined for CD3, Con A and ionomycin+PMA proliferation. Mean values ($\Delta$cpm) are expressed for pretreatment and post-treatment±SEM. There was no change in proliferation at the 100,000 unit dose or with CD3-mediated or ionomycin/PMA activation.

MS is a chronic demyelinating disease of the central nervous system (CNS) that has been postulated to be T cell mediated and autoimmune. Progression or recurrence of immune damage appears to result from a failure of normal regulatory mechanisms to suppress the immune-mediated process in MS. Because CR-EAE is a model T cell mediated, inflammatory autoimmune CNS process that resembles MS and immunoregulation with ingested IFN-α was demonstrated to benefit EAE, it was determined whether ingested IFN-α was non-toxic and had biological effects in subjects with early relapsing-remitting multiple sclerosis. Doses that showed measurable biological effects in normals and insured a complete dose-response evaluation in the MS population. PMNC and serum were obtained by venipuncture from stable relapsing-remitting multiple sclerosis subjects at pretreatment and at two weeks after three per week (Monday, Wednesday, Friday) treatments in a dose escalation trial with washout periods of at least two weeks (n=10 at 10,000, n=9 at 30,000 and n=8 at 100,000 units). PMNC were examined for CD3, Con A and ionomycin+PMA proliferation and induced TGF-β, TNF-α, IL-2, IL-10 and IFN-γ secretion as described above and serum examined for sICAM-1 levels. Con A-mediated proliferation was significantly decreased by ingesting 10,000 ($p<0.01$ by paired t test) and 30,000 units hrIFN-α ($p<0.005$) (FIG. 12). A single patient showed increased Con A proliferative response at both 10,000 and 30,000 units ingested hrIFN-α.

Figure 13:
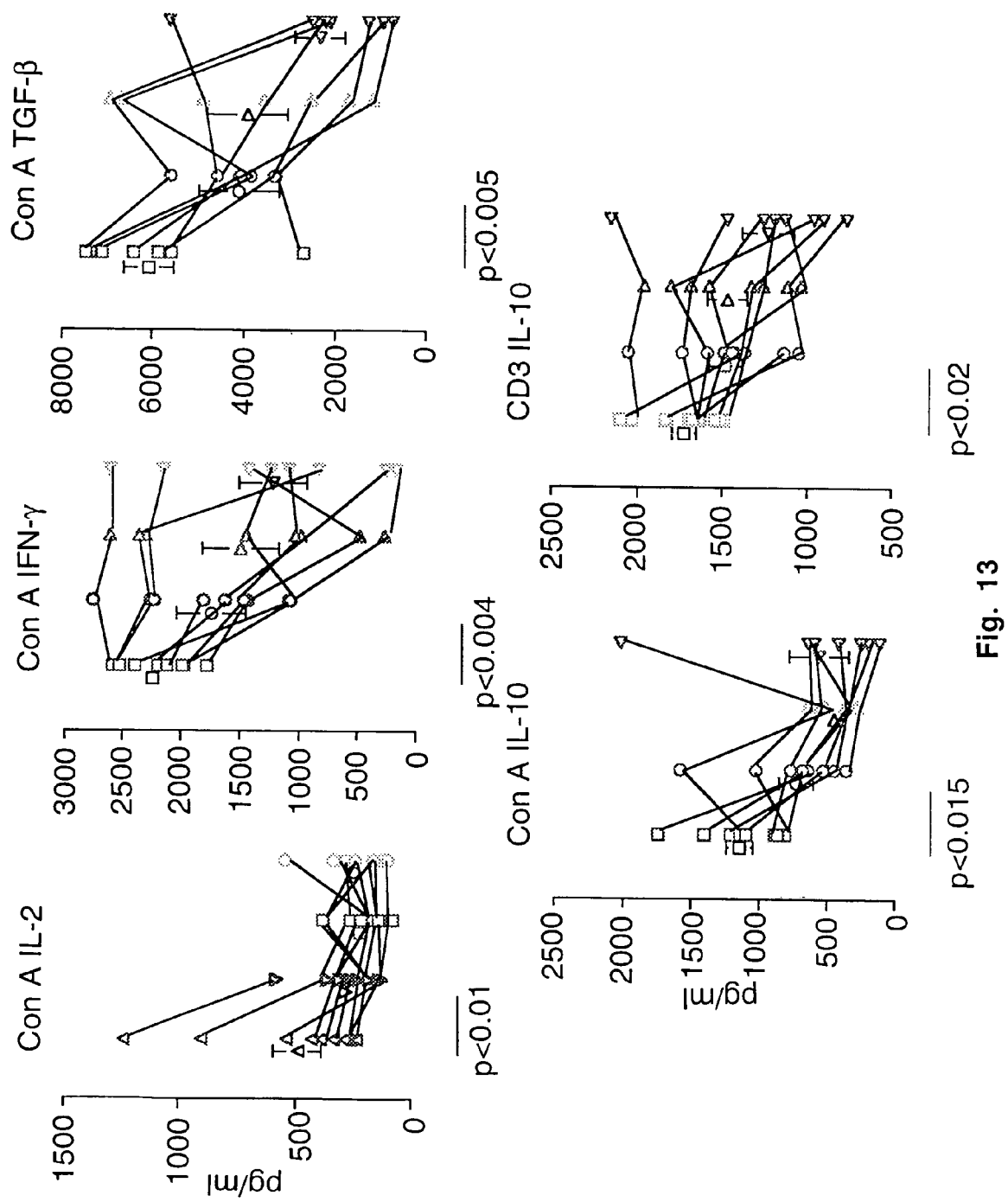
FIG. 13 shows subjects with early relapsing-remitting multiple sclerosis demonstrate decreased Con A-induced I1-2 secretion after ingesting 10,000 units hrIFN-$\alpha$ and decreased Con A-induced IFN-$\gamma$, TGF-$\beta$, IL-10 production, and decreased CD3-induced IL-10 production after ingesting 30,000 units hrIFN-$\alpha$. Drug administration and interleukin assays were performed as outlined in FIGS. 11 and 12. Venipunctures were performed and purified PMNCs examined for CD3, Con A and ionomycin+PMA proliferation and TNF-$\alpha$, IL-2, IL-10 and IFN-$\gamma$ secretion as described above in FIG. 11. To determine the amount of TGF-$\beta$ in cell culture supernatants, the Predicta TGF kit (Genzyme, Cambridge, Mass.) was used. Results are expressed as pg/ml with mean values expressed for pretreatment and post-treatment±SEM as in FIG. 12. IL-4 and IL-6 secretion were not examined in the MS population.
Figure 14:
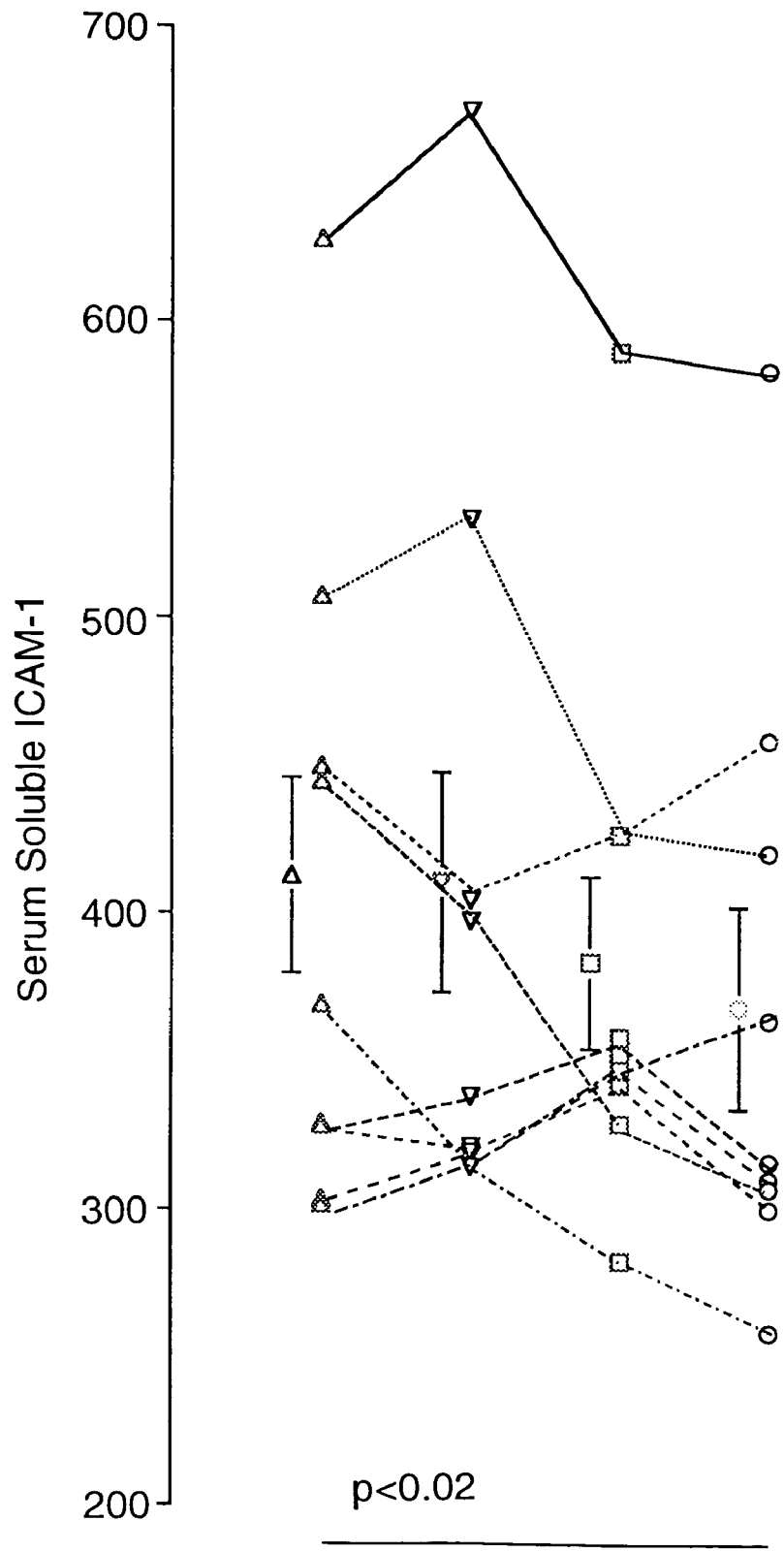
FIG. 14 shows subjects with early relapsing-remitting multiple sclerosis demonstrate decreased soluble ICAM-1 serum (sICAM-1) levels after ingesting 10,000 and 30,000 units hr IFN-$\alpha$. Serum samples were obtained as outlined in FIG. 11. To determine the amount of sICAM-1 in serum samples, the sICAM-1 ELISA kit was used (Bender MedSystems, Vienna, Austria). Results are expressed as prestudy ($\Delta$), after 10,000 ($\nabla$), before 30,000 ($\square$) and after 30,000 (○). Venipuncture was performed one hour after the ingestion of the last drug dose. Mean values (pg/ml) are expressed for pretreatment ($\Delta$) and after 10,000 ($\nabla$), before 30,000 ($\square$) and after 30,000 (○) units±SEM. There was no significant difference between prestudy values and after 10,000 units or before 30,000 units. NS=not significant.

Significant decreased Con A-induced IL-2 secretion ($p<0.01$) was seen after ingesting 10,000 units hrIFN-α and significant decreased Con A-induced IFN-γ ($p<0.004$), TGF-β (n=7) ($p<0.005$), and IL-10 production ($p<0.015$), and CD3-induced IL-10 production ($p<0.02$) were found after ingesting 30,000 units hrIFN-α in subjects with relapsing-remitting multiple sclerosis (FIG. 13). In all relapsing-remitting multiple sclerosis subjects, the pretreatment mean values for cytokine secretion in the dosing cycle following significant decreases did not attain prestudy levels and, a fortiori, were lower than the after-treatment values of the preceding cycle (FIG. 13). Thus, a significant immunomodulatory effect may persist into the next dosing cycle in spite of a washout period. The persistent biological effect of ingested IFN-α was confirmed b y measurement of serum sICAM-1 levels, a direct measure of disease activity that is elevated in MS during clinical relapse or with enhancing lesions on MRI and not liable to potential alteration in vitro. sICAM-1 serum levels declined gradually from prestudy values and were significantly decreased after both 10,000 and 30,000 unit dosing cycles (p<0.02) (FIG. 14), suggesting an effect on subclinical disease.

CD3-stimulated PMNC from relapsing-remitting multiple sclerosis subjects ingesting 30,000 units IFN-α produced less IL-2 after treatment and both Con A and CD3-induced TGF-β secretion were less at 100,000 units (FIG. 13). There was no change in proliferation or secretion of any other cytokine at 100,000 units or changes in TNF-α secretion at any drug dose. Phenotypic analysis disclosed a slight but significant decrease in CD56+/CD3-cells (pre 13.1 vs post 8.0 mean fluorescence intensity, p<0.01) (data not shown). Mixed lymphocyte cultures (MLC) were not altered b y treatment (data not shown).

These results demonstrate that systemic immunobiological effects result from hrIFN-α ingestion of comparatively low doses (10,000-30,000 units). This effect will b e mediated by cells induced to express a type 1 IFN specific-induced Mx mRNA.

EXAMPLE 27

Donor Activated Spleen CD8+ T Cells from IFN Fed Animals, but Not Mock Fed Animals, Can Suppress Actively Induced EAE in Recipients.

Experiments were performed to examine immunomodulation of EAE after passively transferring activated CD4+ and CD8+ T cells from mock fed or mIFN-α fed donors into concurrently actively immunized mice. Five groups of fifteen mice were actively immunized with SCH (day 0+day 7) and mock injected i.p. (day 0) with saline (adjuvant), injected with 107 Con A activated CD4+ or CD8+ spleen cells from mock IFN fed (mock CD8 or mock CD4), or animals fed 10 units mIFN-α for at least 4 weeks (IFN CD4 or IFN CD8) (>90% purity by FACS).

Results from blinded examination performed every two days demonstrated significant differences in clinical outcome in the adjuvant versus IFN CD4 (FIG. 15) (days 14-28; p<0.05 by non-paired t test) and adjuvant versus IFN CD8 (days 14-28; p<0.01 by non-paired t test). There were no significant difference between adjuvant and mock CD4 or mock CD8 at any point. This suggests that donor activated CD4+, and more robustly CD8+ T cells from animals ingesting mIFN-α, but not mock IFN fed animals, can suppress actively induced disease.

EXAMPLE 28

CD8+ T Cells from Mice Ingesting mIFN-α Inhibit Proliferation of Con A Stimulated Splenocytes via Soluble Factor(s).

Figure 16:
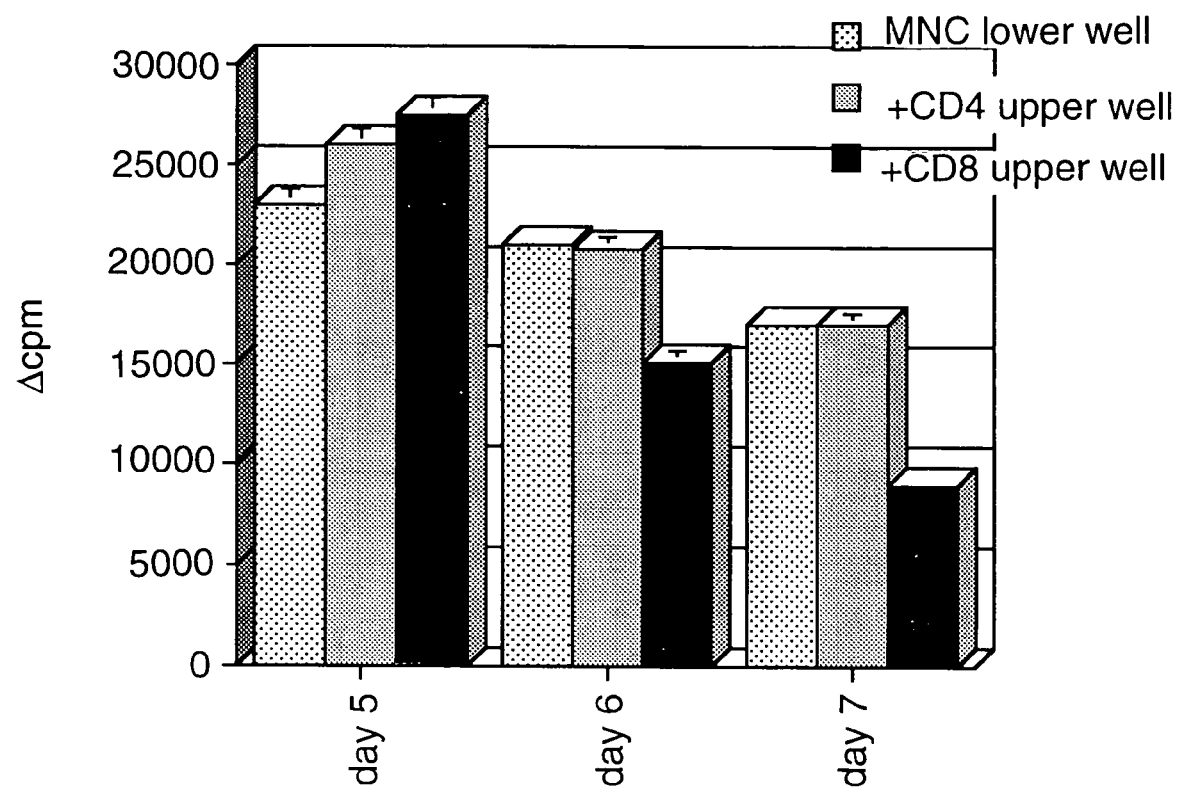
FIG. 16 shows that CD8+ T cells (upper well) from animals ingesting IFN-$\alpha$ inhibit proliferation of Con A splenocytes (lower well)

To evaluate the suppressive effect of CD8+ T cells in EAE mice fed mIFN-α in vitro, pure CD4+ and CD8+ splenocytes populations ($10^5$) (>90% by FACS) from mIFN-α fed mice were stimulated with Con A (50 μg/ml) and placed in the upper well of a transwell plate. Concurrently, Con A (2.5 μg/ml) stimulated splenocytes from EAE immunized non-fed mice ($6\times10^5$) were placed in the bottom well and incubated for 5, 6 or 7 days. On day 5, 6 and 7, Con A-stimulated splenocytes from nonfed mice ($6\times10^5$) (lower well) without upper well cells (baseline control proliferative response) or with $10^5$ Con A stimulated CD4+ or CD8+ spleen cells from animals ingesting mock IFN or mIFN-α (upper well) were transferred to 96 well round bottomed plates in triplicate and pulsed with thymidine for 18 hours. The results (Acpm±SEM) show that b y day 6, Con A stimulated CD8+ T cells from mice ingesting mIFN-α (upper well) inhibited proliferative response of control sample (lower well), whereas Con A stimulated CD4+ T cells (upper well) had no effect (FIG. 16). The inhibitory effect of CD8+ T cells was more profound at seven days incubation. CD8+ T cells apparently secrete a soluble factor that permeates the transwell membrane and inhibits bottom well proliferative responses. Con A stimulated CD4+ or CD8+ T cells from mock fed animals (upper well) showed no inhibition of Con A nonfed splenocytes (lower well) (data not shown). Con A from the upper well itself at high concentrations (50 μg/ml) may inhibit proliferation in the lower well; however Con A at 50 μg/ml with CD4+ T cells in the upper well had no inhibitory effect suggesting that neither CD4+ T cell factors or Con A itself inhibited lower well proliferation. CD4+ T cells may provide immunomodulation by nonsoluble cognate factors not evaluated by the transwell system.

Figure 15:
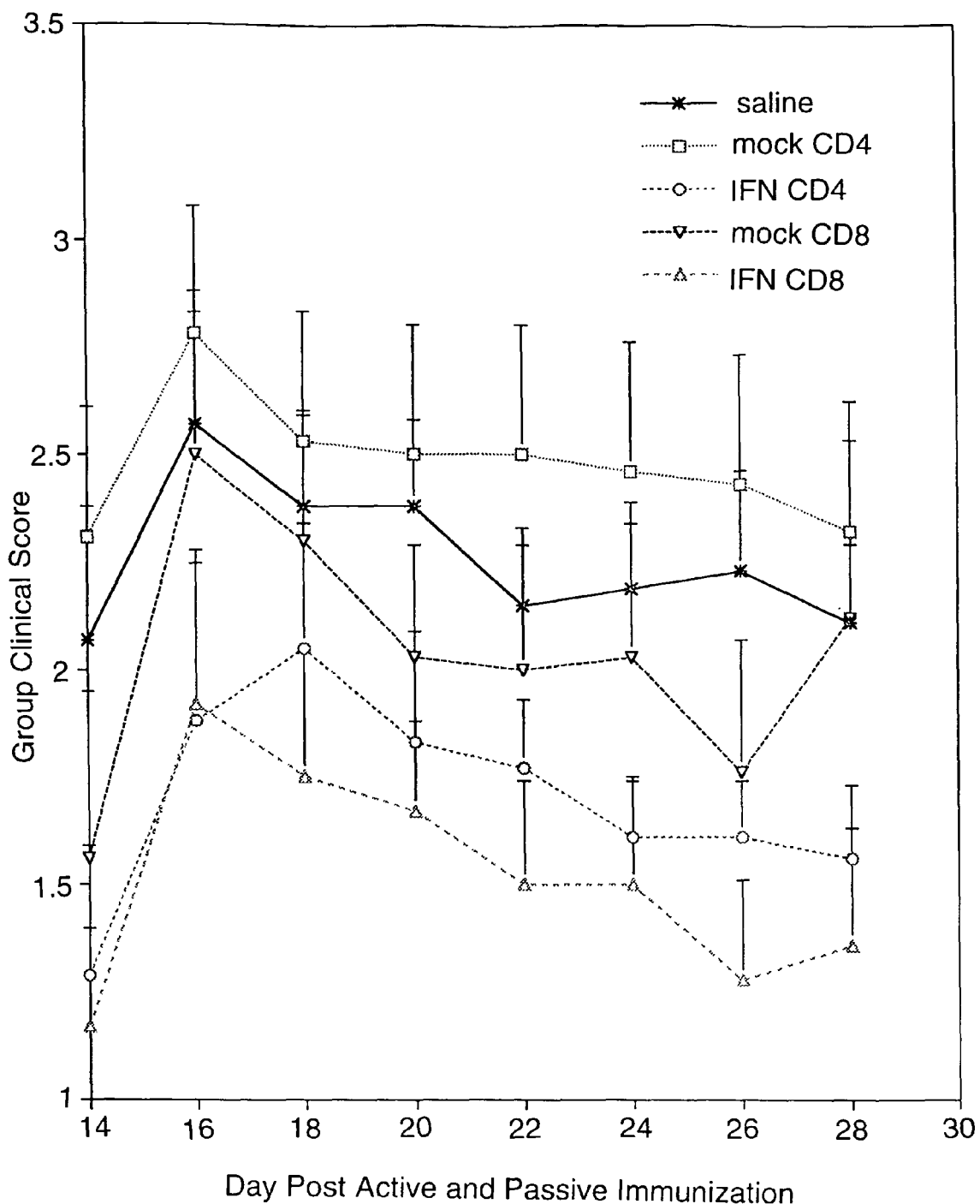
FIG. 15 shows that donor activated spleen CD4+ or CD8+ T cells from IFN fed animals, but not mock fed animals suppresses actively induced EAE in recipients.

These results demonstrate that systemic immunobiological effects result from hrIFN-α ingestion of comparatively low doses (10,000-30,000 units). IFN-α was not detected in serum 1 hour after ingestion of 100,000 units in eight patients with relapsing-remitting multiple sclerosis (human IFN-α ELISA kit, Pestka Biological Laboratories, sensitivity 25 pg/ml {<10 units/ml}. Further, consistent increases in PMNC Mx mRNA expression (a type 1 IFN specific-induced gene) were not demonstrated either in treated normals or MS subjects one hour post dose. Therefore, the biologic effect observed is not dependent on gastrointestinal absorption of the ingested IFN. Several early studies on the pharmacokinetics of IFNs delivered by various routes reported that orally administered IFNs ($6\times10^6$ units) failed to appear in the bloodstream [Cantell et al, 1973; Bocci, 1985; Bocci, 1991]. More recent studies demonstrate that oral administration of IFN-α in mice (>5,000 units/mouse) [Fleischmann et al, 1992], dogs ($3\times10^6$ units/kg) [Gibson et al, 1985], monkeys ($6\times10^6$ units/kg) [Wills et al, 1984], or humans ($1,350\times10^6$ units) [Witt et al, 1992] does not result in detectable levels of IFN-α in the blood. The effect of orally administered IFN cannot be blocked by circulating anti-IFN antibodies in mice [Fleischmann et al, 1992]. This contrasts with parenteral administration, where administered IFN can be measured in the circulation [Gibson et al, 1985; Wills et al, 1984; Radwinski et al, 1987]. These findings strongly suggest that the biologic effect may not require transit of intact IFN across the bowel. The absence of increases in biological protein markers ($\beta_2$-microglobulin, neopterin or 2,5 oligoadenylate synthetase) after oral administration [Witt et al, 1992], but their presence with subcutaneous or intravenous IFN-β [Gibson et al, 1985; Wills et al, 1984; Radwinski et al, 1987; Goldstein et al, 1989] and the data above all suggest that ingested IFN acts through a different mechanism. The neutropenic effect of orally administered IFN can be transferred by injection of blood cells but not by serum to recipient animals [Fleischmann et al, 1992]. In addition, passively transferred mitogen-stimulated splenic T cells from IFN fed animals can suppress disease in actively immunized recipient mice (FIG. 15). Activated monocytes and lymphocytes, by virtue of their ability to circulate through the body, potentially can transfer their biological activities widely in the absence of circulating cytokines after contacting IFN or IFN-induced cells in the GALT [Blalock et al, 1977, 1982; Bocci, 1988].

EXAMPLE 29

Increased Relative IFN-induced Mx mRNA Levels are Found in Mouse Splenocytes After Ingestion of mIFN-α.

Figure 17:
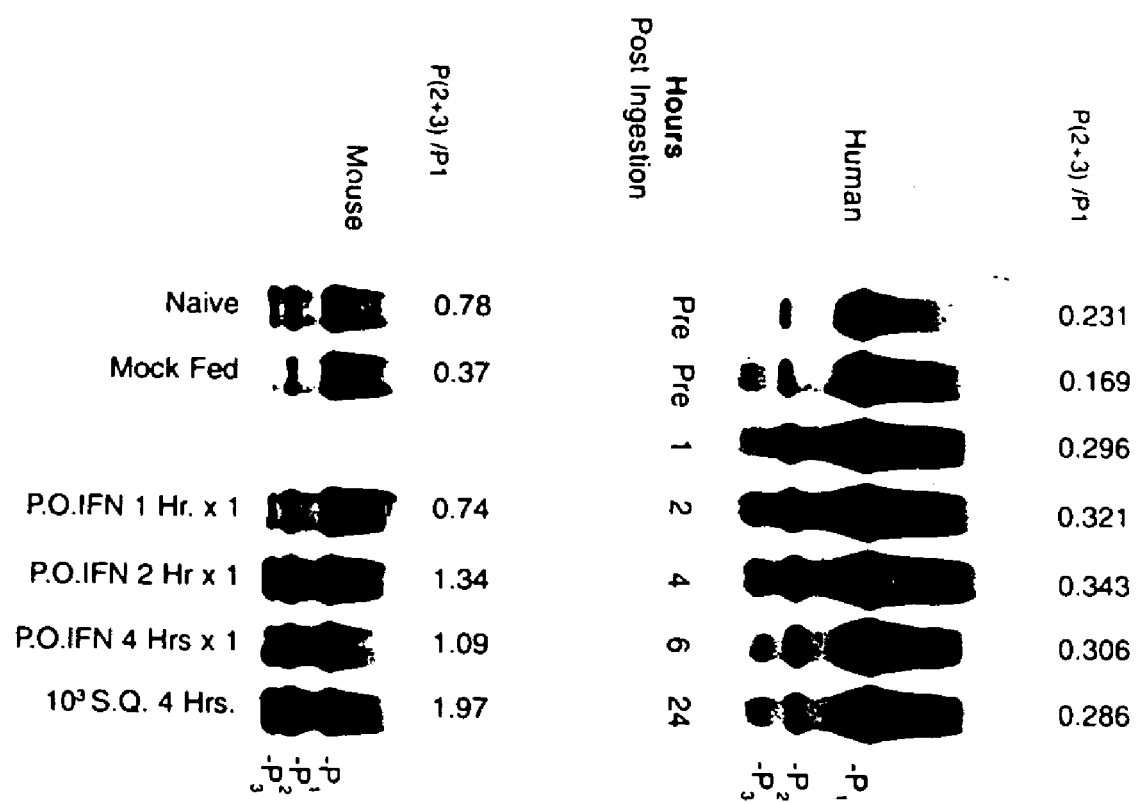
FIG. 17 shows that increased relative IFN-induced Mx mRNA levels are found in mouse and man after ingestion of IFN-$\alpha$.

Mx is a type 1 IFN-specific induced protein that has anti-influenza activity [Horisberger, 1992]. Mx mRNA can potentially be utilized as a sensitive marker for type 1 IFN interaction with lymphoid cells in the GALT. To demonstrate that Mx mRNA signal could be detected in lymphoid cells in the SJL/J mouse (housed in microisolators), specific primer pairs for Mx mRNA and G3PDH, a constitutively expressed mRNA, were developed and the relative levels of mRNA signal were examined using semi-quantitative RT-PCR on splenocytes from naive animals, animals ingesting mock IFN and mIFN-α and a normal human volunteer. mRNA ($5$-$6 \times 10^6$ cells) was isolated from naive (negative control), 1,000 units s.c. mIFN-α (positive control), mock fed, and animals fed 10 units mIFN-α after 1, 2, and 4 hours, and PMNC from a normal human volunteer at baseline, 1, 2, 4, 6, and 24 hours after ingesting 100,000 units hrIFN-α and underwent RT-PCR and hybridization. Using this extremely sensitive method, Mx mRNA was demonstrated constitutively in naive and mock fed animals at low levels and in s.c. injected animals at relatively high levels (FIG. 17). Animals ingesting mIFN-α show inducible levels of Mx mRNA in splenocytes at two hours after ingestion consistently, two times the background levels in naive or mock fed animals. A normal human volunteer demonstrated relative increased MxA mRNA at 4 and 6 hours, but not at 24 hours post ingestion. Ratios of density of the main MxA band (p2) and the differentially spliced secondary MxA band (p3) divided by the G3PDH band (p1) confirm the relative increases in Mx mRNA after IFN ingestion in both mice and man. The rapid appearance of inducible Mx message in splenocytes and PMNC is not surprising in light of the rapid recirculation of lymphocytes [Bocci, 1985; Butcher, 1986] and suggests that ingested IFN-α has distinctive effects on a type 1 mIFN-α-specific inducible signal, even when given via the GI tract in low amounts. This allows a close examination of the specific cells in spleen and MLN (and ultimately within the GALT itself) that interact with ingested IFN.

Ingested IFNs generate relative increased Mx mRNA signals allowing the elucidation of the specific cell types that interact with IFN and transmit its immunomodulatory effect. The present invention in humans shows that ingested IFN has systemically measurable biological effects and modifies subclinical disease activity (lowered sICAM-1 serum levels). The ingestion of biological response modifiers such as IFN-α may be an ideal treatment for autoimmune DM, provides a continuous means of generating immunoregulation that is convenient, active at lower doses and has minimal side effects (non-toxic).

EXAMPLE 30

Isolation of RNA and Preparation of cDNA.

Figure 11:
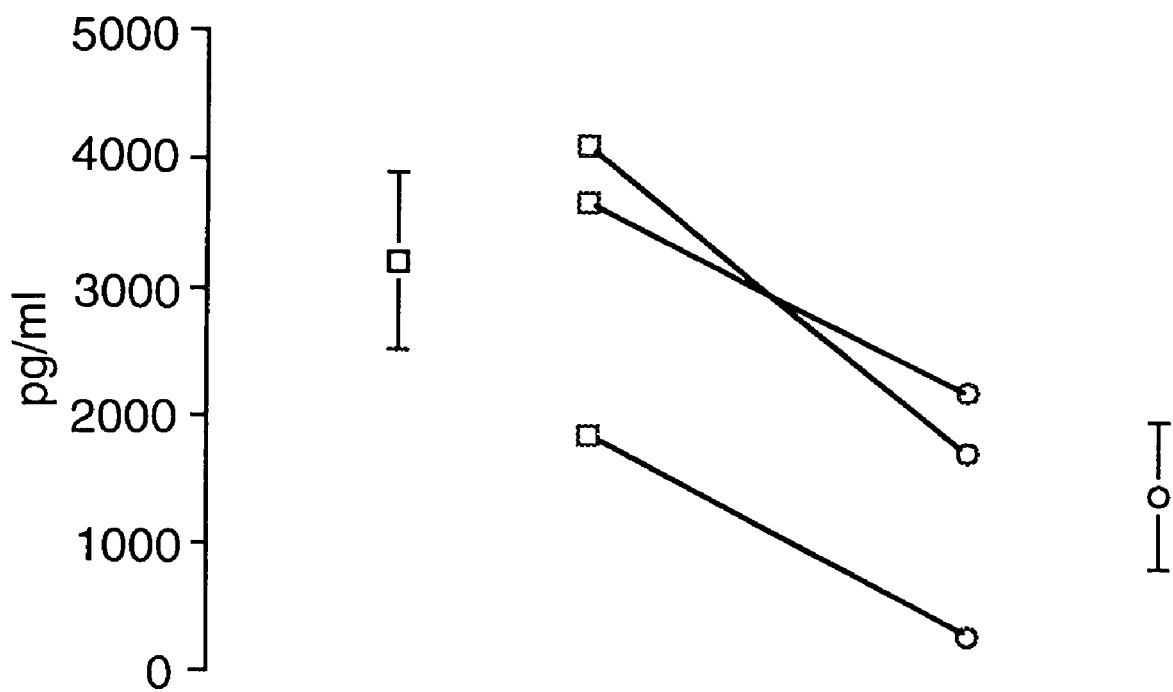
FIG. 11 shows that normal human volunteer subjects ingesting 30,000 units hrIFN-α produce less IFN-γ via the CD3-mediated pathway. Human recombinant IFN-α (hrIFN-α, Roche Pharmaceuticals, Nutley, N.J.) diluted in 5 ml of saline solution, was aliquoted and stored at −70° C. Each dose was thawed, placed in the mouth and immediately swallowed with at least 150 ml of water. PMNC and serum for routine toxicity studies were obtained b y venipuncture from normal healthy controls (three different volunteers at each dose of 300, 1,000, 3,000, 10,000, 30,000 or 100,000 units hrIFN-α, total=18) at pretreatment (□) and after treatment (○). Venipuncture was performed one hour after the ingestion of the last drug dose. Mean values (pg/ml) are expressed for pretreatment (□) and post treatment (○)±SEM. Toxicity studies included: (a) complete blood count with differential and platelet count, prothrombin time, partial thromboplastin time, electrolytes, blood urea nitrogen, creatinine, glucose, albumin, globulin, calcium, magnesium, phosphorus, alkaline phosphatase, γGT, ALT, AST, bilirubin, lactate dehydrogenase, creatine phosphokinase, cholesterol and triglycerides, (b) pregnancy test (if appropriate), (c) urinalysis. Immunological studies including T cell phenotyping and mixed lymphocyte cultures (MLC) were also performed for analysis of biologic effect. PMNC were isolated from heparinized venous blood by means of a Ficoll-Hypaque density gradient (Pharmacia Fine Chemicals, Piscataway, N.J.), washed twice with Hanks balanced salt solution (GIBCO, Grand Island, N.Y.), counted, and resuspended in standard media consisting of 10% fetal calf serum (Whittaker Bioproducts, Walkersville, Md.) in RPMI (Whitaker Bioproducts), with 2% glutamine (GIBCO), and 1% penicillin/streptomycin (GIBCO). PMNC at a final concentration of $2\times10^5/200$ μl in standard tissue culture media were stimulated with a) OKT3 monoclonal antibody form ATCC CRL 8001, Rockville, Md.; ascites diluted to 10 μg/ml in Dulbecco's phosphate buffered saline (DPBS), pH 7.4 and plated for >1 hour at 4° C. in 96 well flat bottom plates, and then washed twice with DPBS, b) Con A at a final concentration of 2.5 μg/ml, or c) ionomycin at 100 ng/ml in combination with myristic acid palmityl ester (PMA) at 1 ng/ml. The plates were incubated in 5% $CO_2$ and humidified atmosphere at 37° C. for three days. Supernatants were collected at 48 hours after activation and frozen at −70° C. after centrifugation for cytokine analysis. The cells for proliferation were pulsed at three days with 2 μCi [$^3$H]-thymidine, harvested 18 hours later on an automated harvester and uptake measured in a Beckman scintillation counter. Results are expressed as stimulated cpm minus background with cells alone±SEM (Δcpm). Interleukins were measured using solid phase ELISA and anti-human interleukin monoclonal antibodies {Anti-IL-2 (Research & Diagnostics, Berkeley, Calif.), anti-IL-4, anti-IL-6, anti-IL-10, anti-TNF-α (all from PharMingen, San Diego, Calif.), anti-IFN-γ (Biomedical Resource, Hatboro, Pa.)} and all samples were run in single batches for each cytokine. Anti-Il-2, anti-IL-4, anti-IL-6, anti-IL-10, antiTNF-α were incubated on polyvinyl plastic 96 well microtiter plates with 0.01 M carbonate buffer, pH 9.6 overnight at 4° C. The plates were blocked with 3% bovine serum albumin in phosphate buffered saline for 3 hours. 100 μl of supernatant in triplicate was added at various dilutions titered to the linear portion of the absorbance/concentration curve and incubated for 1 hour at room temperature. After the plates were washed five times with phosphate buffered saline Tween (0.05%), 100 μl peroxidase conjugated anti-interleukin monoclonal antibody (to a different epitope determinant than the first antibody used to coat the polyvinyl plate) at a 1:1000 concentration was added for 60 minutes. The peroxidase substrate O-phenylenediamine dihydrochloride was added, and the absorbance measured at 450 nm. Standard curves with various amounts of the different interleukins were generated. Informed consent was obtained prior to the beginning of the study from each patient and the protocol was reviewed and approved b y the Committee for the Protection of Human Subjects of UTHSC-Houston. Statistical analysis was performed using paired t test.

PMNC were isolated as described in FIG. 11, counted, aliquoted to Eppendorf tubes, pelleted and lysed in 500 µl lysis solution consisting of 4M guanidine isothiocyanate, 25 mM citrate, 0.5% N-lauroylsarcosine, and 200 mM 2-mercaptoethanol. Lysates were mixed by agitation and stored at −70° C. After thawing, 50 µl of 2 M Na acetate, pH=4, 500 µl of water saturated phenol and 100 µl of chloroform-iso-amyl alcohol (49:1) was added to the lysates. The mixture was then chilled on ice for 15 minutes and spun at 10,000 g for 15 minutes at 4° C. The aqueous phase was removed and RNA precipitated in an equal volume of 2-propanol at −20° C. for 90 minutes. Precipitates were pelleted at 4° C., washed once with 75% alcohol in diethylpyrocarbonate (DEPC)-dd$H_2$O, and repelleted a t 10,000 g at 4° C. for 15 minutes. Vacuum dried pellets were resuspended in 10 µl DEPC-dd$H_2$O containing 2 µg oligo-dT (12-18 mer) and incubated at 65° C. for 10 minutes. After cooling on ice, the mixture was incubated with 10 µl of 2× buffer (100 mM Tris-Cl, pH 8.3, 150 mM KCL, 6 mM Mg$Cl_2$, 20 mM DTT) and 200U of MMLV reverse transcriptase, 1 mM dNTPs, 100 µg/ml acetylated BSA, and 25 U of RNAsin for 60 minutes at 37° C. Tubes were then heated to 95° C. for 5-10 minutes, and 80 µl of dd$H_2$O added to the 20 µl reaction mixture. Samples were stored at 4° C. until further use.

EXAMPLE 31

PCR Conditions:

Cytokine specific primer pairs for the inducible MxA mRNA and the constitutively expressed G3PHD mRNA were designed by JSW and otained from GynSys, the Woodlands, Tex. The primer pairs are complementary to exons separated by at least one intron to avoid unrecognized amplification of cellular DNA and are designated by the relative position in the human mRNA {Mx: Plus strand primer GTGGAGCAG-GACCTGGCCCTG (400-420) (SEQ ID NO: 1); minus strand primer GAGCCTCTGTGGTGGCAATG (895-876) (SEQ ID NO: 2); G3PHD: plus strand primer CAACG-GATTTGGTCGTATTGGGCGC (84-108) (SEQ ID NO: 3); minus strand primer TTACTCCTTGGAGGCCAT-GTGGGCC (1068-1094) (SEQ ID NO: 4)}. 5 µl of cDNA (representing DNA derived from 3-$5 \times 10^6$ cells) was amplified in 0.5 ml Gene-amp reaction tubes (Cetus Corp) in 200 µM final concentration of the four primers, 200 mM dNTPs, 0.5 U of Taq polymerase, and PCR buffer containing 2.5 mM Mg$Cl_2$, 50 mM KCl, 10 mM Tris-Cl pH 8.3, and 0.001% gelatin in a final volume of 25 ml. The reaction mixture was overlaid with a drop of light mineral oil, and PCR performed in a DNA thermal cycler (M.J. Research) for 30 cycles: 60 seconds denaturation at 94° C., 120 seconds annealing at 60° C., and 3 minutes extension at 72° C. The reaction product was visualized by electrophoresis of 20 µl of the reaction mixture at 80 V for 70 minutes in 2% agarose in 0.5 x TBE buffer containing 0.5 mg/ml ethidium bromide. Specificity of the amplified product was validated by the predicted size following transfer to nitrocellulose, hybridization with 3'-digoxigenin-labeled (GENIUS™(5, Boeringer Mannheim, Indianapolis, Ind.) internal oligonucleotide probes (MxA: ACCAGATGCCCTCTGGTGCTG, 405-425 (SEQ ID NO: 5); and GAPDH: CCGTCTCCAGAACATCATC-CCTGCC, 687-663 (SEQ ID NO: 6), and chemiluminescent detection with an alkaline phosphatase-conjugated anti-digoxigenin antibody and [4-methoxy-4-(3-phosphatephenyl) spiro(1,2-dioxetane-(3.2'-adamantane)] substrate (GE-NIUS™(7; Boeringer Mannheim) and exposure for 15 and 30 minutes to X-ray film. The relative amount of MxA and GAPDH message amplified was determined by densitometric analysis of the bands on exposed film.

The biologic effect observed herein is probably not dependent on gastrointestinal absorption of the ingested IFN. Several early studies on the pharmacokinetics of IFNs delivered by various routes reported that orally administered IFNs ($6 \times 10^6$ units) failed to appear in the bloodstream. More recent studies demonstrate that oral administration of IFN-α in mice (>5,000 units/mouse), dogs ($3 \times 10^6$ units/kg), monkeys ($6 \times 10^6$ units/kg), or humans ($1,350 \times 10^6$ units) does not result in detectable levels of IFN-α in the blood. The effect of orally administered IFN cannot be blocked by circulating anti-IFN antibodies in mice. This contrasts with parenteral administration, where administered IFN can be measured in the circulation. These findings strongly suggest that the biologic effect may not require transit of intact IFN across the bowel. The absence of increases in biological protein markers ($\beta_2$-microglobulin, neopterin or 2,5 oligoadenylate synthetase) after oral administration, but their presence with subcutaneous or intravenous IFN-β3 and the data above all suggest that ingested IFN acts through a different mechanism, such as an interaction with type I IFN receptors on GALT. The neutropenic effect of orally administered IFN can be transferred by injection of blood cells but not by serum to recipient animals. In addition, passively transferred mitogen-stimulated splenic T cells from IFN fed animals can suppress disease in actively immunized recipient mice. Activated monocytes and lymphocytes, by virtue of their ability to circulate through the body, potentially can transfer their biological activities widely in the absence of circulating cytokines after contacting IFN or IFN-induced cells in the gut associated lymphoid tissue (GALT).

The present invention in humans demonstrates that ingested IFN has systemically measurable biological effects and may modify subclinical disease activity. The ingestion of biological response modifiers such as IFN-α potentially provides a continuous means of generating immunoregulation that is convenient, active at lower doses with minimal side effects, and may provide enhanced efficacy via unique and potent immunoregulatory circuits in the GALT. The oral route may circumvent potential therapeutic limitations associated with neutralizing antibodies to injected type I IFNs in subjects with MS and other diseases.

EXAMPLE 32

NOD Mouse—inhibition of Spontaneous Disease:

Non-obese diabetic (NOD) female four—eight week old mice were obtained from Taconic Farms, maintained and fed under pathogen-free conditions in microisolators, and handled under negative pressure sterile hoods. Surveillance animals were maintained with experimental animals and examined regularly for routine murine pathogens. Diabetes (blood sugar >11.1 mmol/l; >200 mg/ml) occured in 50% of naive or mock fed female NOD mice by age 19 weeks in our facility.

Ten units of murine natural IFN-α (mIFN-α) (Cytimmune mouse IFN-α, $4.0 \times 10^5$ IRU/ml, Lee Biomolecular Research, Inc., San Diego, Calif.), or mock murine IFN-α (Cytimmune <2 IRU/ml, Lee Biomolecular Research, Inc., San Diego, Calif. (generated identically to IFN-α/β except cultures are mock induced)) was administered using a 2.5 cm syringe fitted with a 22-24 gauge ball point needle (Thomas Scientific, Swedesboro, N.J.) every other day or daily to NOD mice beginning at age five or nine weeks and continuing until blood glucose was positive for two consecutive determinations. Untreated (mock fed with saline) and unfed (naive) mice showed no differences in the onset or proportion of diabetes and were combined for purposes of analysis. IFN-α was directly delivered to the distal esophagus, stomach and proximal small intestine bypassing the oropharynx (as determined experimentally by injecting Evans blue during routine feeding and subsequent sacrifice). Mock murine IFN control was used. This is not a conditioned media, but rather a preparation identical to the IFN preparation except it is not induced with Newcastle disease virus (according to Lee Biomolecular). Therefore the mock murine preparation has whatever normal cell components are contained in the Newcastle disease virus-induced preparation. Inactivated IFN preparation denatured by trypsin and 2-ME and boiling was not used. Although this procedure may denature disulfide linkages and break the the intact molecule, it remains problematic whether this method for in vitro use would work in the model where very low amounts are administered in vivo. In addition, alterations in the secondary and tertiary structure of IFN may itself induce an immune response, with subsequent immunosuppression.

These animals were followed after initiation of feeding by weekly blood glucose determination (Life Scan One Touch II, Johnson & Johnson) beginning at week 10. Animals were considered diabetic if two consecutive blood glucose determinations were above >11.1 mmol/l. Disease course was plotted as Kaplan-Meier curve with the y axis denoting the % remaining non-diabetic mice.

The animals were sacrificed after blood sugar >11.1 mmol/l, and pancreases were harvested, fixed in 10% formalin, embedding in paraffin, sectioned at 5 microns, and stained with H/E. Pancreases were scored by a pathologist blinded to the treatment groups. Coded slides were read by light microscopy. Islet inflammation (insulinitis) was graded 0 to 4, according to the extent of peri-and intra-islet infiltration by mononuclear cells: 0=none; 1=peri-islet leucocytes without islet infiltration; 2=<25% islet area infiltrated by leucocytes; 3=25-75% islet area infiltrated; and 4=>75% islet area infiltrated. A mean insulinitis score was calculated for each pancreas by dividing the sum of the insulinitis score for individual islets by the number of islets examined (>40/pancreas) (Miller, B., et al. 1988).

EXAMPLE 33

Measurement of Cytokine Secretion:

Individual spleens were aseptically removed and single cell suspensions were prepared by passage through a 90 μm stainless wire meshes. Red cell lysis was performed in the spleen cell suspensions with 2 mls of ACK solution added to the pellet and the reaction allowed to continue at 5 minutes at room temperature. Suspensions were washed three times in Dulbecco's PBS, then stimulated with Con A at a final concentration of 2.5 μg/ml (Sigma Chemical Co., St Louis, Mo.) or ionomycin at 100 ng/ml (Calbiochem, La Jolla, Calif.) in combination with myristic acid palmityl ester (PMA) at 1 ng/ml (Sigma Chemical Co., St. Louis, Mo.) for 48 hours with $2 \times 10^6$ cells/ml in 96 well U-bottomed plates in a humidified 5% $CO_2$/95% air incubator at 37° C. Interleukins was measured using solid phase ELISA. Murine IL-1, IL-2, IL-4, IL-6, IL-10, IFN-γ kits (Biosource International, Camirillo, Calif.), TNF-α and TGF-β kits (Genzyme, Cambridge, Mass.) were utilized.

Statistical analysis was performed using Mann Whitney test or and one-tailed student's t-test for parametric data or Mann Whitney rank sum test for nonparametric data.

EXAMPLE 34

Figure 18:
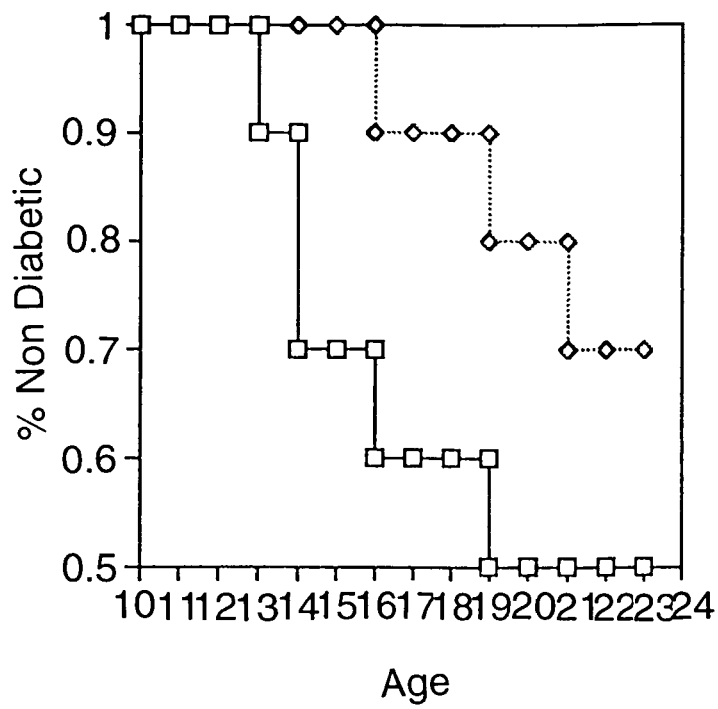
FIG. 18 shows that every other day ingestion (oral) mIFN-$\alpha$ from age nine weeks suppresses the incidence of diabetes mellitus in NOD mice. Twenty NOD female mice were obtained from Taconic Farms at eight weeks of age and feeding with mock IFN (n=10) or 10 units mIFN-$\alpha$ (n=10) three times per week was initiated at nine weeks. Animals were followed by venipuncture for blood glucose>11.1 mmol/l. Data was analysed for time to overt diabetes in each group by Kaplan Meier survival curve with % nondiabetic vs age. Animals were followed for 23 weeks in total. Animals fed IFN-$\alpha$ ($\square$) demonstrated delayed onset of IDDM and decreased frequency of animals becoming diabetic compared to untreated (○) animals (p<0.02 by Mann Whitney test).
Figure 19:
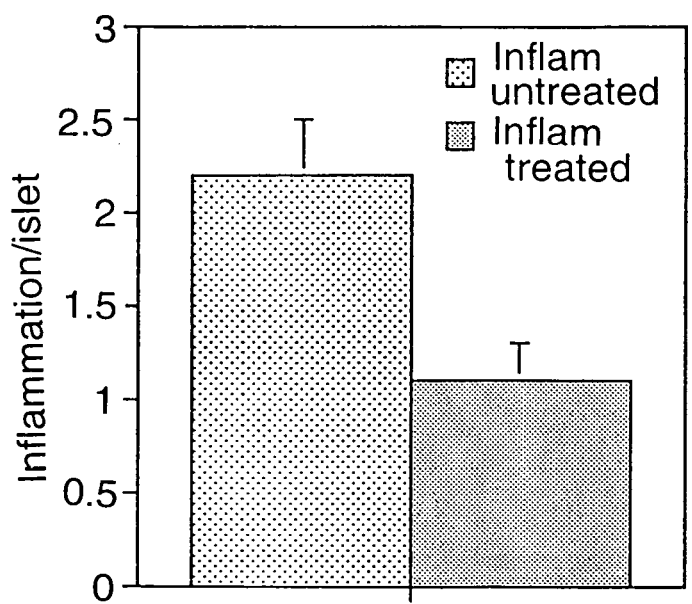
FIG. 19 demonstrates that every other day ingestion (oral) mIFN-$\alpha$ from age nine weeks decreases the grade of islet inflammation. Pancreases were evaluated by a blinded pathologist after removal, fixing in 10% formalin, embedding in paraffin, sectioned at 5 microns, and stained with H/E.

Ingested (Oral) mIFN-α Suppresses IDDM in NOD Mice:

In the first set of experiments, twenty NOD female mice were obtained from Taconic Farms at eight weeks of age and were untreated (naive or fed with mock IFN) (n=10) or treated with 10 units mIFN-α (n=10) every other day starting at nine weeks. Animals were followed weekly for 13 weeks in total for elevated serum glucose by venipuncture. Data was analysed for time to overt diabetes in each group by Kaplan Meier survival curve with % nondiabetic vs age. Animals treated orally with mIFN-α demonstrated delayed onset of IDDM and a decreased frequency of diabetes compared to untreated animals (p<0.02 by Mann Whitney rank sum test) (FIG. 18). There was also a decreased grade of islet inflammation in the treated versus the untreated group (untreated 2.2±0.3 {n=8} vs treated 1.1±0.2 {n=8}, p<0.01 by t test) (FIG. 19).

Figure 20:
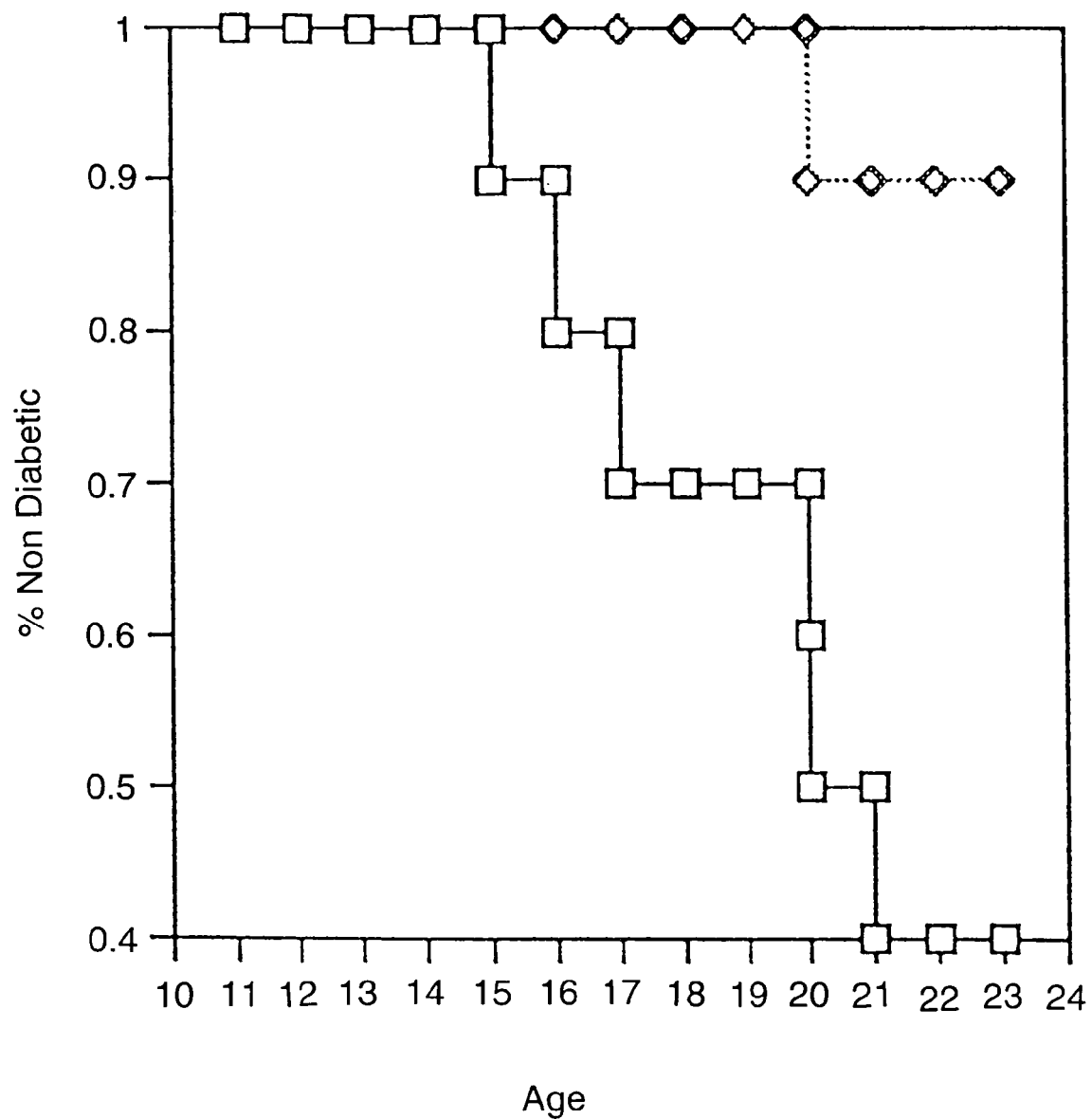
FIG. 20 shows that every day ingestion (oral) mIFN-$\alpha$ from age nine weeks enhances the suppression of diabetes mellitus in NOD mice. Twenty NOD female mice were obtained from Taconic Farms at eight weeks of age and feeding with mock IFN (n=10) or 10 units mIFN-$\alpha$ (n=10) every day was initiated at nine weeks. Animals were followed by venipuncture for blood glucose>11.1 mmol/l. Data was analysed for time to overt diabetes in each group by Kaplan Meier survival curve with % nondiabetic vs age. Animals were followed for 23 weeks in total. Animals fed IFN-$\alpha$ ($\square$) demonstrated significantly greater delayed onset of IDDM and decreased frequency of animals becoming diabetic compared to untreated (○) animals (p<0.002 by Mann Whitney test).

In a second set of experiments, another twenty NOD female mice at eight weeks of age were untreated (naive or fed with mock IFN) (n=10) or treated with 10 units mIFN-α (n=10) every day starting at nine weeks and followed as described above. Data was again analysed for time to overt diabetes in each group b y Kaplan Meier survival curve with % nondiabetic vs age. Animals treated with oral mIFN-α demonstrated a more significant delay in onset of IDDM and decreased frequency of diabetes compared to untreated animals (p<0.01 by Mann Whitney rank sum test) (FIG. 20).

Figure 21:
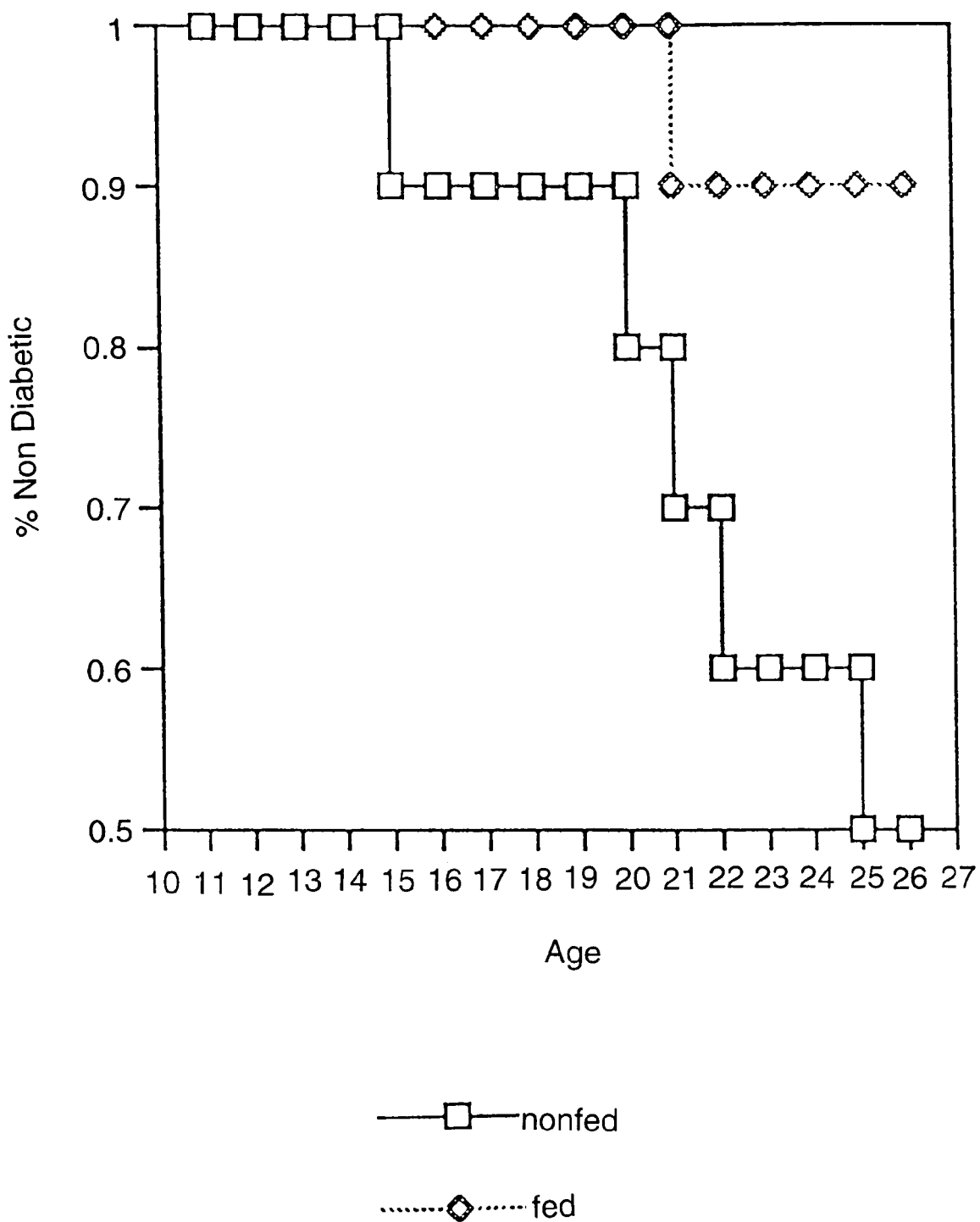
FIG. 21 demonstrates that every other day ingestion (oral) mIFN-$\alpha$ from age five weeks suppresses the incidence of diabetes mellitus in NOD mice. Sixteen NOD female mice were obtained from Taconic Farms at eight weeks of age and feeding with mock IFN (n=8) or 10 units mIFN-$\alpha$ (n=8) every other day starting at five weeks of age was initiated. Animals were followed as described above. Animals fed IFN-$\alpha$ ($\square$) demonstrated significantly greater delayed onset of IDDM and decreased frequency of animals becoming diabetic compared to untreated (○) animals (p<0.002 by Mann Whitney test).

A third set of experiments examined whether every day feedings starting at an earlier age (five weeks) further enhanced the therapeutic effect of ingested mIFN-α. Twenty 4 week old NOD female mice were untreated (naive or fed with mock IFN) (n=8) or treated with 10 units mIFN-α (n=8) every other day starting at five weeks of age. Animals were followed for 21 weeks in total. Animals treated orally with mIFN-α demonstrated significantly greater delayed onset of IDDM and decreased frequency of diabetes compared to the untreated group (p<0.002 by Mann Whitney rank sum test) (FIG. 21). The results from FIGS. 18 and 21 suggest that every other day treatment with ingested mIFN-α initiated at five weeks is more effective than treatment at a later stage in the NOD mouse model.

EXAMPLE 35

Figure 22A:
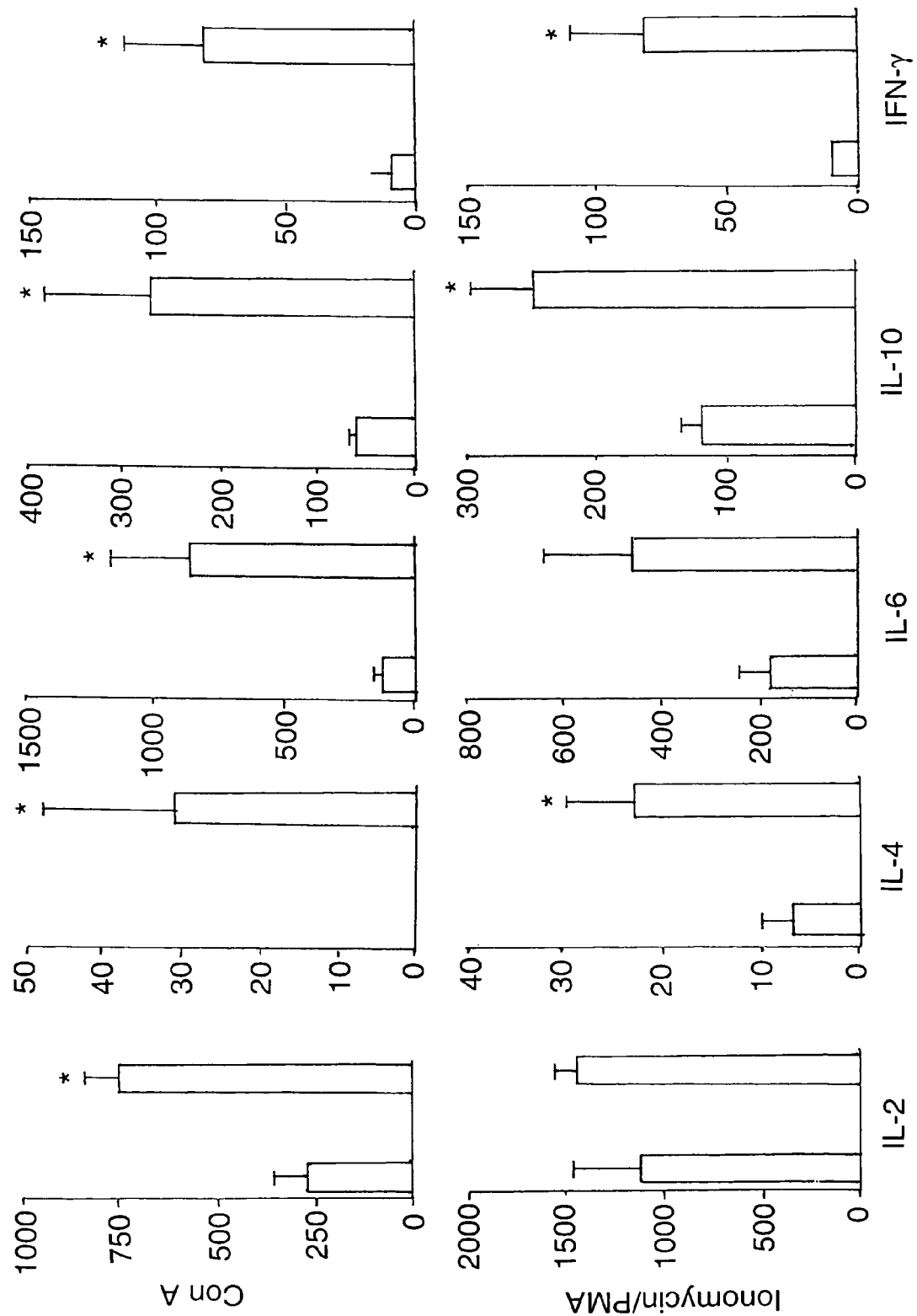
FIG. 22 demonstrates that ingested mIFN-$\alpha$ increases the mitogen-induced production of IL-2, IL-4, IL-6, IL-10 and IFN-$\gamma$ in spleen cells. Splenocytes from individual animals were stimulated with Con A or ionomycin+PMA. Cytokines was measured using solid phase commercial ELISA. Individual data correspond to animals mock fed IFN-$\alpha$ ($\square$) or animals fed with 10 units mIFN-$\alpha$ (○). Con A: untreated versus treated IL-2-p<0.025; IL-4-p<0.05; IL-6-p<0.02; IL-10-p<0.04; IFN-$\gamma$-p<0.05; TNF-$\alpha$-p<0.15, TGF-$\beta$-p<0.32, IL-1-p<0.08. Ionomycin+PMA: untreated versus treated IL-2-p<0.21; IL-4-p<0.05; IL-6-p<0.07; IL-10-p<0.015; IFN-$\gamma$-p<0.03; TNF-$\alpha$-p<0.4, TGF-$\beta$-p<0.24; IL-1-p<0.25.
Figure 22B:
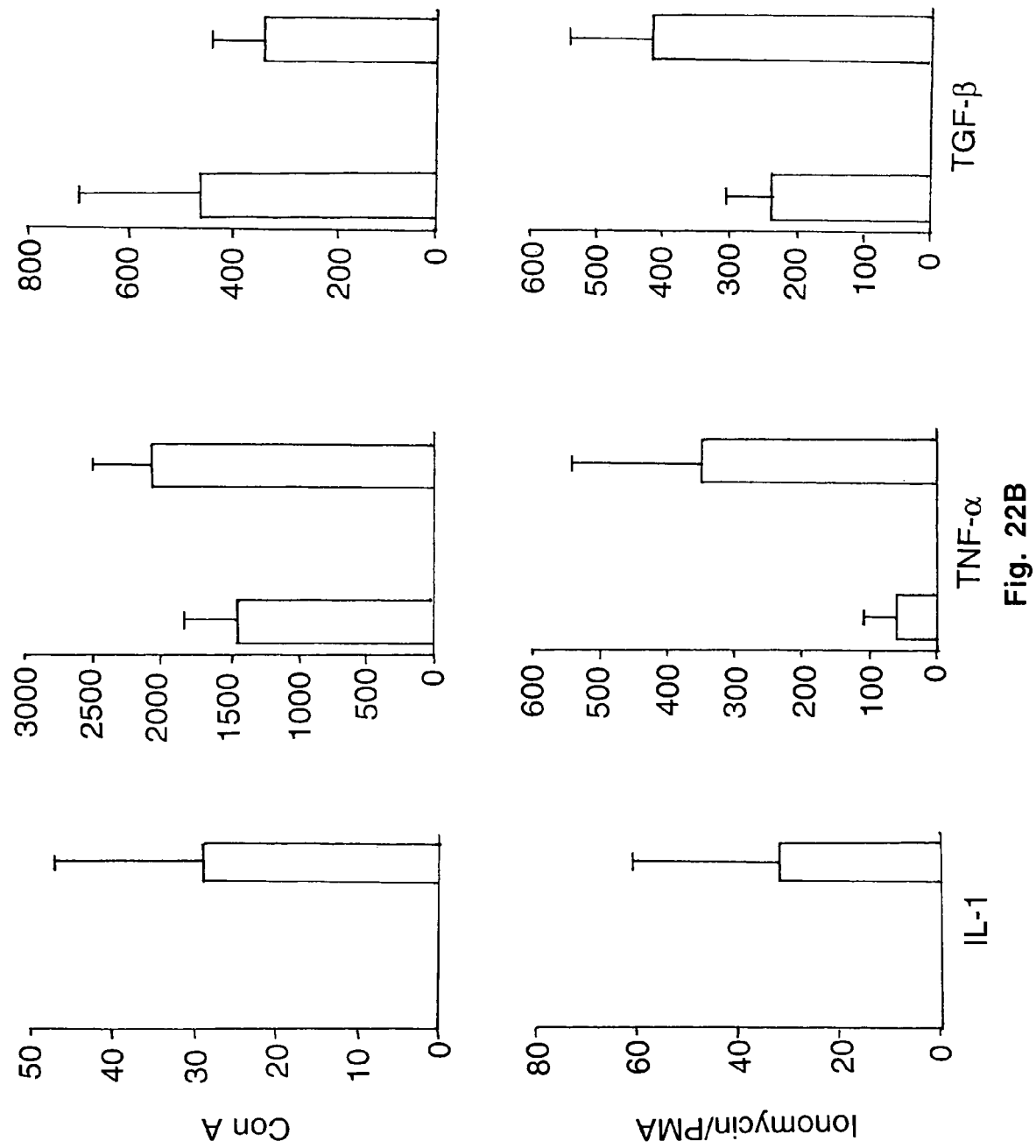

Ingested mIFN-α Increases the Mitogen-induced Production of IL-2, IL-4, IL-6, IL-10 and IFN-γ in Spleen Cells:

The cytokine profiles of Con A and ionomycin/PMA stimulated spleen cells in untreated versus oral mIFN-α treated mice were compared. Whole splenocytes from non-diabetic mice from experiment #2 were stimulated with Con A and ionomycin/PMA and IL-1, IL-2, IL-4, IL-6, IL-10, IFN-γ, TNF-α and TGF-β was measured. Splenocytes from IFN—Y treated mice showed increased production of IL-2, IL-4, IL-6, IL-10 and IFN-γ after Con A stimulation and increased production of IL-4, IL-10 and IFN-γ after ionomycin/PMA stimulation (FIG. 22). There were no changes in Con A or ionomycin/PMA stimulated TNF-α (FIG. 22*b*), IL-1 and TGF-β secretion (FIG. 22*c*) comparing untreated and IFN-α treated mice.

The ingestion of the biological response modifier IFN-α is an ideal treatment for autoimmune DM, providing a continuous means of generating immunoregulation that is convenient, active at lower doses with minimal side effects (non-toxic), optimally effective given early in the disease course and providing enhanced efficacy via unique and potent immunoregulatory circuits in the GALT. Human IDDM is preceded by a long presymptomatic period—suggesting that the clinical symptoms of disease arise only after the destruction of the majority of b cells. Ingested IFN-α is no doubt applicable to human IDDM as an effective therapy administered at a pre-clinical asymptomatic stage during vulnerable periods in at-risk populations (non-diabetic relatives of IDDM patients with anti-64 kDa autoantibodies including the 65 kD isoform, high titers of islet cell antibodies (ICA), and insulin autoantibodies (IAA), in multiplex families).

EXAMPLE 36

Rheumatoid Arthritis Open Label Phase I Study

Subjects. Patients with RA (n=4) were used (table 1). Recruitment of the subjects with clinically stable RA was from patients in the rheumatology clinics of the University of Texas-Houston Medical School. All patients met American College of Rheumatology (ACR) criteria for the diagnosis of RA (Arnett, 1988). Informed consent was obtained prior to the beginning of the study from each patient and the protocol was reviewed and approved b y the Committee for the Protection of Human Subjects of UTHSC-Houston.

Clinical evaluation: A symptom-directed physical examination and complete rheumatologic examination was performed at two week intervals during the entire trial including: (a) standard painful (PJ) and swollen joint (SJ) counts, both patient and physician global assessment of disease activity (on a visual analog scale) and duration of morning stiffness (MS); (b) blood tests including CBC, differential and platelet count, PT, PTT, SMAC-19 and CPK; (c) pregnancy test (if appropriate); (d) urinalysis; and (e) rheumatoid factor (RF), erythrocyte sedimentation rate (ESR) (Westergren method), anti-nuclear antibody (ANA), and thyroid function tests including TSH, $T_4$, and anti-peroxidase antibody levels. The specific endpoint was a 25% decrease in signs or symptoms of joints as defined by joint count (PJ, SJ), duration of morning stiffness (MS), patient or physician global assessment of disease activity, and ESR at eight weeks (exit) following entry into the study.

Drug Administration. Thirty thousand units of human recombinant IFN-α (hrIFN-α: ROFERON™, Roche Pharmaceuticals, Nutley, N.J.) was diluted in 5 ml of saline solution, aliquoted and stored at −70° C. The dose of ingested IFN-α in RA was based on the optimal biological modifying dose of IFN-α in a previous study in multiple sclerosis patients (Brod, 1997). Each dose was thawed, placed in the mouth and immediately swallowed with at least 150 ml of water. Four subjects with RA were administered hrIFN-α for eight weeks at 30,000 units every other day.

Cell Preparation. Peripheral blood mononuclear cells (PMNC) and sera were obtained by venipuncture at entry, every two weeks during the study and at exit. PMNCs were isolated from heparinized venous blood by means of a Ficoll-Hypaque density gradient (Pharmacia Fine Chemicals, Piscataway, N.J.), washed twice with Hanks balanced salt solution (GIBCO, Grand Island, N.Y.), counted, and resuspended in standard media consisting of 10% fetal calf serum (FCS) (Whittaker Bioproducts, Walkersville, Md.) in RPMI (Whitaker Bioproducts, Walkersville, Md.), with 2% glutamine (GIBCO), and 1% penicillin/streptomycin (GIBCO). PMNCs at a final concentration of $2 \times 10^{5/200}$ μl in standard tissue culture media described above were unstimulated, stimulated with OKT3 monoclonal antibody (ATCC CRL 8001, Rockville, Md.; ascites diluted to 10 mg/ml in DPBS pH=7.4 and plated for ≧1 hour at 4° C. in 96 well flat bottom plates (Costar, Cambridge, Mass.), and then washed×2 with DPBS), or Con A at a final concentration of 2.5 μg/ml (Sigma Chemical Co., St Louis, Mo.). The plates were incubated in 5% $CO_2$ and humidified atmosphere at 37° C. for two days and supernatants frozen at −70° C. for future analysis.

Measurement of cytokine and serum soluble intercellualer adhesion molecules. Interleukins were measured using solid phase ELISA assay and anti-human interleukin mAb. Anti-IL-1β, anti-IL-2, anti-IL-4, anti-IL-6, anti-IL-8, anti-IL-10, IL-12p40, IL-12p70, anti-IFN-γ, anti-TNF-α, anti-TGF-β (Research & Diagnostics, Berkeley, Calif.) mAbs were used and ELISA performed as outlined in (Brod, 1996). To determine the amount of serum soluble ICAM-1 and sVCAM-1 in serum samples, the sICAM-1 and sVCAM-1 ELISA kits were used (Bender MedSystems, Vienna, Austria).

TABLE 1

Patient Demographics

| Patient | age | sex | years RA | present Rx | past Rx |
|---|---|---|---|---|---|
| C. W. | 67 | female | 7 | prednisone 10 mg/d, Tolectin 400 qd | SSZ, MTX, AZA, minocycline |
| J. N. | 55 | female | 7 | aspirin 3.9 g/d | SSZ, HQ, oral gold, MTX |
| A. S. | 36 | female |  | prednisone 10 mg/d, ibuprofen 2,400 qd |  |
| P. L. | 49 | female | 13 | prednisone 7.5 mg/d, DMSO, ibuprofen 800 tid | MTX, oral gold |

EXAMPLE 36

Rheumatoid Arthritis Results

Ingested hrIFN-α was not toxic at any dose used as measured by routine blood chemistries, thyroid tests or urinalysis. There were no consistent changes in ANA or RF titers. One patient (C.W.) experienced a 25% worsening of four clinical indices over the course of the trial while also improving in two other clinical indices (table 2). The other three patients improved in at least three of six clinical and laboratory indices measured. Overall, of the 24 possible clinical and laboratory disease indices measured, there were 12 indices that improved by at least 25% and 4 that worsened by 25%, all the worsening in one patient (table 2). This suggests that ingested hrIFN-α is probably not clinically toxic in RA.

Figure 23:
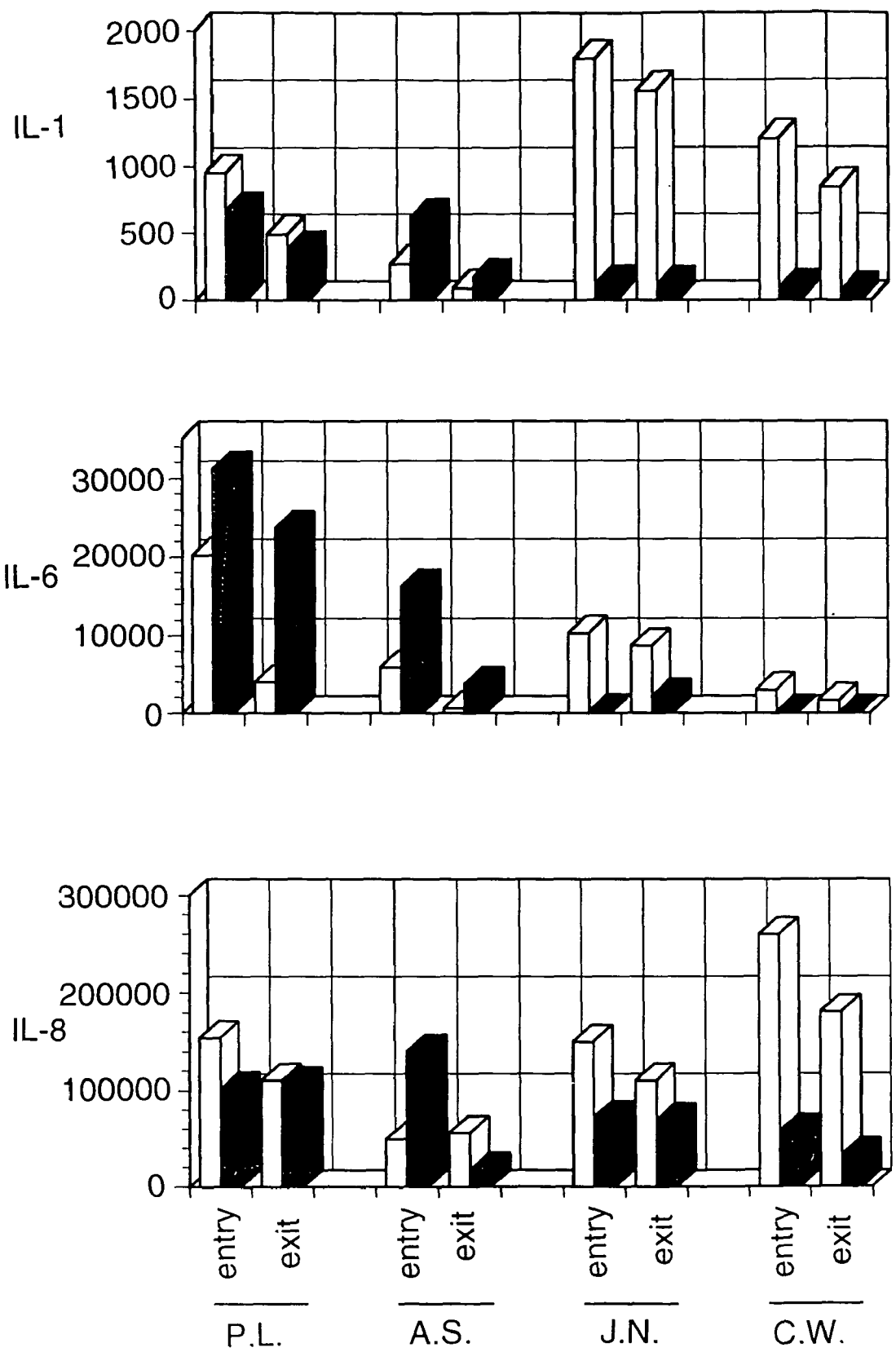
FIG. 23 illustrates that subjects with RA demonstrate decreased CD3- and Con A-activated IL-1$\beta$ (top), IL-6 (middle), and IL-8 (bottom) PMNC secretion after ingesting 30,000 units hrIFN-$\alpha$. PMNC from RA subjects were taken immediately before initiation of treatment (entry) and one hour after the last dose of ingested IFN-$\alpha$ after eight weeks on treatment (exit). CD3 (white bars) and Con A (black bars) are shown for all four patients. Results are expressed as pg/ml with mean values expressed for entry and exit.

Next it was determined whether ingested IFN-α modified biological responses in subjects with RA. Decreased CD3-induced IL-1 secretion was seen from PMNC after ingesting hrIFN-α in all four patients and after Con A activation in two of four patients comparing entry and exit samples (FIG. 23A). There was no increase in IL-1 secretion in any patient. There was also decreased CD3-induced IL-6 secretion after ingesting hrIFN-α in all four patients and after Con A activation in two of four patients (FIG. 23B). One patient (JN) demonstrated increased Con A-induced IL-6 secretion without affecting her clinical improvement during the trial. There was also decreased CD3-induced IL-8 secretion after ingesting hrIFN-α in two patients and after Con A activation in three of four patients (FIG. 23C).

No patient experienced increased IL-8 secretion at exit. Two patients (C. W. and J. N.) also had IL-8 cytokine analysis performed on 48 hour unstimulated PMNCs. These two patients showed at least a 75% reduction in the spontaneous secretion of IL-8 secretion at exit compared to entry (CW: 39,150 pg/ml entry vs 9,840 pg/ml exit; JN: 15,850 pg/ml entry vs 1,620 pg/ml exit). This confirmed the decreased IL-8 with CD3- or Con A-activated PMNCs. The effect of ingested IFN-α on serum soluble ICAM-1 and VCAM-1 levels was also measured, but no consistent changes after ingestion of hrIFN-α were detected. There were no other consistent alterations of CD3 or Con A secretion of IL-2, IL-4, IL-10, IL-12p40, IL-12p70, IFN-γ, TGF-β or TNF-α.

TABLE 2

Clinical and Laboratory Evaluation

| patient | study point | ESR | Patient Global Assess | Physician Global Assess | Painful Joints | Swollen Joints | Morning Stiffness |
|---|---|---|---|---|---|---|---|
| C. W. | entry | 21 | 23 | 24 | 17 | 22 | 45 |
|  | exit | 55+ | 72+ | 53+ | 7* | 28+ | 30* |
| J. N. | entry | 57 | 25 | 28 | 5 | 17 | 15 |
|  | exit | 61 | 16* | 6* | 0* | 14 | 2* |
| A. S. | entry | 49 | ND | 25 | 5 | 11 | ND |
|  | exit | 29* | ND | 6* | 4 | 8* | ND |
| P. L. | entry | 61 | 28 | 34 | 27 | 30 | 60 |
|  | exit | 48 | 28 | 22* | 13* | 13* | 60 |

Examination at entry into the trial and exit from the trial was performed that included standard painful (PJ) and swollen joint (SJ) counts, both patient and physician global assessment of disease activity, duration of morning stiffness (MS), and erythrocyte sedimentation rate (ESR) (Westergren method). A 25% decrease in scores from entry to exit is designated by asterick (*) and 25% increase in scores is designated by cross (+) from entry to exit.

EXAMPLE 37

Ingested hrIFN-α has Definable Biological Effects in Humans with Auto-immune Disease.

The small numbers of RA patients (n=4) precluded statistical analysis in this exploratory study, however there was a trend toward inhibition of CD3- and Con A-mediated IL-1, IL-6, and IL-8 secretion after eight weeks of every other day ingested hrIFN-α. Although one patient did experience worsening of clinical and laboratory indices, the other three patients experienced improvement in at least three separate clinical or laboratory indices. These results demonstrate that systemic immunobiological effects result from hrIFN-α ingestion of comparatively low doses (30,000 units) in subjects with RA. Oral IFN has also shown modulatory effects in animal models of RA including collagen-induced arthritis (CIA) and adjuvant arthritis (AA) in rats (Yoshino, 1995; Yoshino, 1996).

Substantial amounts of IL-1 and IL-6 are found in RA (Firestein, 1990). In animal models of RA, IL-1 administered into the joint may induce arthritis (Pettipher, 1986), inflammatory changes (Chandrasekhar, 1990), and induces leucocyte infiltration into the synovial lining and synovial fluid (Libert, 1990); McIntosh, 1989). There is a striking correlation between levels of IL-1 in rheumatoid synovial fluid and disease activity (Eastgate, 1988; Kahle, 1992). Enhanced in vitro IL-1 generation by circulating monocytes is temporally linked to an early event in the onset of exacerbation of RA (Shore, 1986).

IL-6, produced by T and B cells, is a proinflammatory cytokine detected at increased levels in RA synovial tissue (Field, 1991; Helle, 1991; Houssiau, 1988; Hirano, 1988]. Synovial fluid IL-6 levels correlate with ESR in patients with inflammatory arthritis (Waage, 1989) and IL-6 can induce bone resorption (Ishimi, 1990).

Interleukin-8 (IL-8), a potent chemotactic and proadhesive mediator for PMNCs, plays a key role in amplifying and perpetuating inflammation. IL-8 recruits inflammatory cells into the joint (Loetscher, 1994; Leirisalo-Repo, 1994). IL-8/NAP-1 is the major T-cell chemoattractant in RA-synovium (Nishiura, 1996) and is secreted by T cells (Wechsler, 1994). RA PMNCs are activated to produce proinflammatory IL-8 mRNA peripherally before entering the synovium (Schulze-Koops, 1997). Methotrexate (MTX) treatment inhibits PMNC IL-8 synthesis that is correlated with clinical improvement (Seitz, 1995).

The rationale for treatment of RA by ingested IFN-α is that a proportion of RA patients will eventually develop destructive joint disease. The goal of therapy is to provide an agent that is readily accepted by patients, that is non-toxic so that it can be considered for use in the earliest stage of the disease process, is administered frequently without inconvenience, may prevent destructive phase of the disease, and neither induce nor be abrogated by the presence of circulating IFN neutralizing antibodies.

Oral type I IFNs satisfy these requirements. Type I IFNs are general immunomodulators, are acid stable and resist preprandial stomach acidity. The biologic effect observed is dependent on gastrointestinal absorption of the ingested hrIFN-α. Oral administration of IFN-α in humans (1,350× $10^6$ units) (Witt, 1992) does not result in detectable levels of IFN-α in the blood. Activated monocytes and lymphocytes, by virtue of their ability to circulate through the body, potentially can transfer their biological activities widely in the absence of circulating cytokines after contacting IFN or IFN-induced cells in the gut associated lymphoid tissue (GALT) (Ford, 1969); Butcher, 1996). Type I IFNs are capable of producing target organ-blind immunomodulation without respect to immunogenetic background or inciting antigen. Early treatment of RA with ingested IFN-α prevents or retards progression of RA via the reduction of inflammatory cytokine production.

All patents and publications mentioned in this specification are indicative of the levels of those skilled in the art to which the invention pertains. Any patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

Arnett, F., et al., *Arthritis Rheum*, vol. 31, pp. 315-24, 1988.
Bocci V, et al., 1985. Int. J. Pharmaceutics 46: 199-202.
Bocci V. 1988. J. Biol. Res. Mod. 4:340-352.
Bocci V. 1991. Clin. Pharmacokinet. 21:411-417.
Brod, S., et al., *Multiple Sclerosis—Clinical and Laboratory Research*, vol. 3, pp. 1-7 (1997).
Brod, S. A., et al., *Neurology*, vol. 46, pp. 1633-1638, 1996.
Butcher E C., Curr. Topics in Microbiol. Immunol. 1986; 128:85-122.
Cantell K, et al., 1973. J. Gen. Virol. 20: 97-104.
Cruikshank, B., *Ann Rheum Dis*, vol. 13, pp. 136-146, 1954.
Gibson D M, et al., 1985. J. Int. Res. 5:403-408.
Goldstein D, et al., 1989. J. Natl. Cancer Inst. 81:1061-1068.
Fleischmann W R, et al., Proc. Soc. Exp. Biol. Med 1992; 201:199-207.
Horisberger M A., 1992. Mx protein: Function and mechanism of action in: Interferon: Principles and medical applications. S. Baron, et al., Eds. (UTMB Press, Galveston, Tex., 1992), pp. 215-224.
Larocca A P, et al., 1989. J. Int. Res. 9, suppl. 1, S51-60.
Miller, B., et al. 1988. Both. J Immunol 140:52-58.
Radwanski E, et al., 1987. J Clin Pharmaco. 27: 432-435.
Wills R J, et al., 1984. J. Int. Res. 4:399-409.
Witt P J, et al., 1992. J. Int. Res. 12:411-413.
Firestein and N. Zvaifler, *Arthritis Rheum*, vol. 33, pp. 768-73, 1990.
Pettipher, E., et al., *Proc Natl Acad Sci USA*, vol. 83, pp. 8749-8753, 1986.
Chandrasekhar, S., et al., *Clin Immunol Immunopath*, vol. 55, pp. 382-400, 1990.
Libert, C., et al., *Eur J Immunol*, vol. 20, pp. 691-694, 1990.
McIntosh, J., et al., *J Immunol*, vol. 143, pp. 162-167, 1989.
Eastgate, J., et al., *Lancet*, vol. September 24, pp. 706-709, 1988.
Kahle, P., et al., *Ann Rheum Dis*, vol. 51, pp. 731-734, 1992.
Shore, A., et al., *Clin Exp Immunol*, vol. 65, pp. 293-302, 1986.
Field, M. et al., *Rheumatol Int*, vol. 11, pp. 45-50, 1991.
Helle, M., et al., *J Immunol Methods*, vol. 11, pp. 47-56, 1991.
Houssiau, F., et al., *Arthritis Rheumatism*, vol. 31, pp. 784-788, 1988.
Hirano, T., et al., *Eur J Immunol*, vol. 18, pp. 1797-1801, 1988.
Waage, A., et al., *Clin Immunol Immunopath*, vol. 50, pp. 394-398, 1989.
Ishimi, Y., et al., *J Immunol*, vol. 145, pp. 3297-3303, 1990.
Loetscher, P., et al., *Cytokine*, vol. 6, pp. 162-170, 1994.
Leirisalo-Repo, M., *Pharmacology & Toxicology*, vol. 75, pp. 1-3, 1994.
Nishiura, H., et al., *Clinical Immunology & Immunopathology*, vol. 80, pp. 179-84, 1996.
Wechsler, A., et al., *Journal of Immunology*, vol. 1531, pp. 2515-23, 1994.
Schulze-Koops, H., et al., *Arthritis & Rheumatism*, vol. 40, pp. 639-47, 1997.
Seitz, M., et al., *British Journal of Rheumatology*, vol. 34, 1995.
Witt, P. J., et al., *J Interferon Res*, vol. 12, pp. 411-413, 1992.
Ford W. and J. Gowan, *Semin Hematol*, vol. 6, pp. 67-83, 1969.
Butcher E. and L. Picker, *Science*, vol. 272, pp. 60-66, 1996.

What is claimed is:

1. A method of preventing destructive joint disease associated with rheumatoid arthritis in a human individual with an earlier stage of rheumatoid arthritis comprising:
   orally administering about 50 I.U./kg to about 25,000 I.U./kg of IFN-α to said individual; and
   immediately swallowing said IFN-α.

2. The method of claim 1, wherein about 30,000 units of IFN-α is orally administered.

3. The method of claim 1, wherein said IFN-α is administered every other day.

4. The method of claim 1, wherein said IFN-α is human recombinant interferon.

5. A method of reducing inflammation associated with rheumatoid arthritis in a human individual with rheumatoid arthritis comprising:
   orally administering about 50 I.U./kg to about 25,000 I.U./kg of IFN-α to said individual; and
   immediately swallowing said IFN-α.

6. The method of claim 5, wherein about 30,000 units of IFN-α is orally administered.

7. The method of claim 5, wherein said IFN-α is administered every other day.

8. The method of claim 5, wherein said IFN-α is human recombinant IFN-α.

9. A method of reducing a level of an interleukin in a human individual with rheumatoid arthritis, comprising:
   orally administering about 50 I.U./kg to about 25,000 I.U./kg of IFN-α to said individual; and
   immediately swallowing said IFN-α, thereby reducing the level of IL-1, IL-6, IL-8, or a combination thereof in said individual.

10. The method of claim 9, wherein about 30,000 units of IFN-α is orally administered.

11. The method of claim 9, wherein said IFN-α is administered every other day.

12. The method of claim 9, wherein said IFN-α is human recombinant IFN-α.

* * * * *

UNITED STATES PATENT AND TRADEMARK OFFICE
CERTIFICATE OF CORRECTION

| | |
|---|---|
| PATENT NO. | : 7,790,153 B2 |
| APPLICATION NO. | : 10/801277 |
| DATED | : September 7, 2010 |
| INVENTOR(S) | : Staley Brod |

Page 1 of 1

It is certified that error appears in the above-identified patent and that said Letters Patent is hereby corrected as shown below:

In title page, item (54) Title, line 1 and column 1, line 1, delete "METHOD" and insert --METHODS-- therefor.

In title page, item (63) Related U.S. Application Data, line 2, after "abandoned," insert --which is a continuation-in-part of application No. 08/844,731, filed on Apr. 21, 1997, now abandoned, which is a continuation-in-part of application No. 08/631,470, filed on Apr. 12, 1996, now abandoned, which is a continuation-in-part of application No. 08/408,271, filed on Mar. 24, 1995, now abandoned, which is a continuation-in-part of application No. 08/226,631, filed on Apr. 12, 1994, now abandoned--.

Signed and Sealed this
Eighth Day of March, 2011

David J. Kappos
*Director of the United States Patent and Trademark Office*